(12) United States Patent
Goryshin et al.

(10) Patent No.: US 7,067,644 B2
(45) Date of Patent: Jun. 27, 2006

(54) DOUBLE TRANSPOSITION METHODS FOR MANIPULATING NUCLEIC ACIDS

(75) Inventors: Igor Yu Goryshin, Madison, WI (US); Todd A Naumann, State College, PA (US); William S Reznikoff, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 563 days.

(21) Appl. No.: 10/007,483

(22) Filed: Dec. 5, 2001

(65) Prior Publication Data

US 2002/0132349 A1 Sep. 19, 2002

Related U.S. Application Data

(60) Provisional application No. 60/251,482, filed on Dec. 5, 2000.

(51) Int. Cl.
*C12N 15/11* (2006.01)
*C07H 21/04* (2006.01)

(52) U.S. Cl. .................................... 536/23.1; 435/24.1
(58) Field of Classification Search ............... 536/29.1, 536/23.1
See application file for complete search history.

(56) References Cited

U.S. PATENT DOCUMENTS

| 5,925,545 A | 7/1999 | Reznikoff et al. |
| 5,948,622 A | 9/1999 | Reznikoff et al. |
| 5,965,443 A | 10/1999 | Reznikoff et al. |
| 6,159,736 A | 12/2000 | Reznikoff et al. |
| 6,294,385 B1 | 9/2001 | Goryshin et al. |
| 6,406,896 B1 * | 6/2002 | Reznikoff et al. .......... 435/183 |

FOREIGN PATENT DOCUMENTS

| WO | WO 98/10077 | 3/1998 |
| WO | WO 00/17343 | 3/2000 |

OTHER PUBLICATIONS

Resnikoff, Ann. Rev. Microl., 47:945-963, 1993.*

Bhasin, A., et al., "Hairpin Formation in Tn5 Transposition," *The Journal of Biological Chemistry* 52:37021-37029 (1999).
Goryshin, I.Y. et al. "Tn5/IS50 Target Recognition," *Proc. Natl. Acad. Sci. USA* 95:10716-10721 (1998).
Goryshin, I.Y., et al., "Tn5 in Vitro Transposition," *the Journal of Biological Chemistry* 273:7367-7374 (1998).
Hoffman, L.M., "Transposome Insertional Mutagenesis and Direct Sequencing of Microbial Genomes," *Genetica* 108:19-24 (2000).
Magarshak, Y., "Double Transpositions and the Secondary Structures of RNA," *Biophysics* 38:913-914 (1993).
Sakai, J., et al., "Identification and Characterization of a Pre-cleavage Synaptic Complex that is an Early Intermediate in Tn10 Transposition," *The EMBO Journal* 14:4374-4383 (1995).
Davies, D. R., et al., "Three-Dimensional Structure of the Tn5 Synaptic Complex Transposition Intermediate," *Science* 289:77-85 (2000).
Naumann Todd A. and William S. Reznikoff, "Trans catalysis in Tn5 Transposition," *PNAS* 97:8944-8949 (2000).
Pollack, Andrew Selling Evolution in Ways Darwin Never Imagined, *The New York Times* Oct. 28, 2000.
Ostermeier, Marc et al., "A combinatorial approach to hybrid enzymes independent of DNA homology," *Nature Biotechnology* 17:1205-1209 (1999).
Zhou M & Reznikoff WS, Tn5 transposase mutants that alter DNA binding specificity, J. Mol. Biol. 271:362-373 (1997).
Zhou M et al., Molecular genetic analysis of transposase-end DNA sequence recognition: cooperativity of three adjacent base-pairs in specific interaction with a mutant Tn5 transposase, J. Mol. Biol. 276:913-925 (1998).

* cited by examiner

*Primary Examiner*—Nancy Vogel
(74) *Attorney, Agent, or Firm*—Quarles & Brady LLP

(57) ABSTRACT

Methods are provided for manipulating nucleic acid to produce gene fusions, to delete or clone a portion of a chromosome, or to insert a sequence into a chromosome. The methods employ sequential transposition processes using two or more pairs of inverted repeat transposase-interacting sequences on a transposable polynucleotide wherein each pair of transposase-interacting sequences interacts with a distinct transposase enzyme.

8 Claims, 10 Drawing Sheets

Screen for chromosomal deletions.

Replica Plate Individual Colonies.

TYE     SM4     SM5

$SM4^r + SM5^r$ = No transposition $SM4^s + SM5^r$ = Transposition event: Inversion or 'wrong' deletion $SM4^s + SM5^s$ = Transposition event: Deletion

SEQUENCE LISTING

<160> NUMBER OF SEQ ID NOS: 10

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: LINKER A
      (FULL LENGTH)

<400> SEQUENCE: 1
ctgtctcttg atcagatcta cttgtgtata agagtcag                              38

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: LINKER A
      (COMPRESSED)

<400> SEQUENCE: 2
ctgtctcttg atcagatgtg tataagagtc ag                                    32

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: LINKER B
      (FULL LENGTH)

<400> SEQUENCE: 3
ctgtctcttg atcagatcta gatgtgtata agagacag                              38

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: LINKER B
      (COMPRESSED)

<400> SEQUENCE: 4
ctgtctcttg atcagatgtg tataagagac ag                                    32

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: PRIMER FWD2

<400> SEQUENCE: 5
cagatctcat gcaagcttga gctc                                             24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: PRIMER

<400> SEQUENCE: 6
ggtctgcttt ctgacaaact cgggc                                            25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: PRIMER

<400> SEQUENCE: 7
acgcgaaata cgggcagaca tggcc    25

<210> SEQ ID NO 8
<211> LENGTH: 3277
<212> TYPE: DNA
<213> ORGANISM: Artificial Sequence
<220> FEATURE:
<223> OTHER INFORMATION: Description of Artificial Sequence: Pgt4

<400> SEQUENCE: 8

| | | | | | |
|---|---|---|---|---|---|
| gacagctgtc | tcttgatcag | atctcatgca | agcttggctg | caggggggggg | gggaaagcca | 60 |
| cgttgtgtct | caaaatctct | gatgttacat | tgcacaagat | aaaaatatat | catcatgaac | 120 |
| aataaaactg | tctgcttaca | taaacagtaa | tacaaggggt | gttatgagcc | atattcaacg | 180 |
| ggaaacgtct | tgctcgaggc | cgcgattaaa | ttccaacatg | gatgctgatt | tatatgggta | 240 |
| taaatgggct | cgcgataatg | tcgggcaatc | aggtgcgaca | atctatcgat | tgtatgggaa | 300 |
| gcccgatgcg | ccagagttgt | ttctgaaaca | tggcaaaggt | agcgttgcca | atgatgttac | 360 |
| agatgagatg | gtcagactaa | actggctgac | ggaatttatg | cctcttccga | ccatcaagca | 420 |
| ttttatccgt | actcctgatg | atgcatggtt | actcaccact | gcgatcccrg | ggaaaacagc | 480 |
| attccaggta | ttagaagaat | atcctgattc | aggtgaaaat | attgttgatg | cgctggcagt | 540 |
| gttcctgcgc | cggttgcatt | cgattcctgt | ttgtaattgt | ccttttaaca | gcgatcgcgt | 600 |
| atttcgtctc | gctcaggcgc | aatcacgaat | gaataacggt | ttggttgatg | cgagtgattt | 660 |
| tgatgacgag | cgtaatggct | ggcctgttga | acaagtctgg | aaagaaatgc | ataagctttt | 720 |
| gccattctca | ccggattcag | tcgtcactca | tggtgatttc | tcacttgata | accttatttt | 780 |
| tgacgagggg | aaattaatag | gttgtattga | tgttggacga | gtcggaatcg | cagaccgata | 840 |
| ccaggatctt | gccatcctat | ggaactgcct | cggtgagttt | tctccttcat | tacagaaacg | 900 |
| gcttttttcaa | aaatatggta | ttgataatcc | tgatatgaat | aaattgcagt | ttcatttgat | 960 |
| gctcgatgag | ttttttctaat | cagaattggt | taattggttg | taacactggc | agagcattac | 1020 |
| gctgacttga | cgggacggcg | ctttgttga | ataaatcgaa | cttttgctga | gttgaaggat | 1080 |
| cagatcacgc | atcttcccga | caacgcagac | cgttccgtgg | caaagcaaaa | gttcaaaatc | 1140 |
| accaactggt | ccacctacaa | caaagctctc | atcaaccgtg | gctccctcac | tttctggctg | 1200 |
| gatgatgggg | cgattcaggc | ctggtatgag | tcagcaacac | cttcttcacg | aggcagacct | 1260 |
| cagcgccccc | cccccctgc | aggtcgactc | tagaggatcc | ccgggtaccg | agctcgaatt | 1320 |
| cagatctgat | caagagacag | ctgtcgacgt | caggtggcac | ttttcgggga | aatgtgcgcg | 1380 |
| gaacccctat | ttgtttattt | ttctaaatac | attcaaatat | gtatccgctc | atgagacaat | 1440 |
| aaccctgata | aatgcttcaa | taatattgaa | aaaggaagag | tatgagtatt | caacatttcc | 1500 |
| gtgtcgccct | tattcccttt | tttgcggcat | tttgccttcc | tgttttttgct | cacccagaaa | 1560 |
| cgctggtgaa | agtaaaagat | gctgaagatc | agttgggtgc | acgagtgggt | tacatcgaac | 1620 |
| tggatctcaa | cagcggtaag | atccttgaga | gttttcgccc | cgaagaacgt | tttccaatga | 1680 |

-continued

```
tgagcacttt taaagttctg ctatgtggcg cggtattatc ccgtattgac gccgggcaag    1740
agcaactcgg tcgccgcata cactattctc agaatgactt ggttgagtac tcaccagtca    1800
cagaaaagca tcttacggat ggcatgacag taagagaatt atgcagtgct gccataacca    1860
tgagtgataa cactgcggcc aacttacttc tgacaacgat cggaggaccg aaggagctaa    1920 ccgcttttt gcacaacatg ggggatcatg taactcgcct tgatcgttgg aaccggagc    1980 tgaatgaagc cataccaaac gacgagcgtg acaccacgat gcctgtagca atggcaacaa    2040
cgttgcgcaa actattaact ggcgaactac ttactctagc ttcccggcaa caattaatag    2100
actggatgga ggcggataaa gttgcaggac cacttctgcg ctcggccctt ccggctggct    2160
ggtttattgc tgataaatct ggagccggtg agcgtgggtc tcgcggtatc attgcagcac    2220
tggggccaga tggtaagccc tcccgtatcg tagttatcta cacgacgggg agtcaggcaa    2280
ctatggatga acgaaataga cagatcgctg agataggtgc ctcactgatt aagcattggt    2340
aactgtcaga ccaagtttac tcatatatac tttagattga tttaaaactt catttttaat    2400
ttaaaaggat ctaggtgaag atcctttttg ataatctcat gaccaaaatc ccttaacgtg    2460
agttttcgtt ccactgagcg tcagaccccg tagaaaagat caaaggatct tcttgagatc    2520 cttttttct gcgcgtaatc tgctgcttgc aaacaaaaaa accaccgcta ccagcggtgg    2580
tttgtttgcc ggatcaagag ctaccaactc tttttccgaa ggtaactggc ttcagcagag    2640
cgcagatacc aaatactgtc cttctagtgt agccgtagtt aggccaccac ttcaagaact    2700
ctgtagcacc gcctacatac ctcgctctgc taatcctgtt accagtggct gctgccagtg    2760
gcgataagtc gtgtcttacc gggttggact caagacgata gttaccggat aaggcgcagc    2820
ggtcgggctg aacggggggt tcgtgcacac agcccagctt ggagcgaacg acctacaccg    2880
aactgagata cctacagcgt gagctatgag aaagcgccac gcttcccgaa gggagaaagg    2940
cggacaggta tccggtaagc ggcagggtcg gaacaggaga gcgcacgagg gagcttccag    3000
ggggaaacgc ctggtatctt tatagtcctg tcgggtttcg ccacctctga cttgagcgtc    3060
gatttttgtg atgctcgtca ggggggcgga gcctatggaa aaacgccagc aacgcggcct    3120
ttttacggtt cctggccttt tgctggcctt ttgctcacat gttctttcct gcgttatccc    3180
ctgattctgt ggataaccgt attaccgcct ttgagtgagc tgataccgct cgccgcagcc    3240
gaacgaccga gcgcagcgag tcagtgagcg aggaagc                              3277
```

<210> SEQ ID NO 9
<211> LENGTH: 7814
<212> TYPE: DNA
<213> ORGANISM: Artificial Sequence
<220> FEATURE:
<223> OTHER INFORMATION: Description of Artificial Sequence: Pgt7

<400> SEQUENCE: 9

```
gacagctgtc tcttgatcag atctcatgca agcttcagct cactcactca agatgtgtat      60
aagagacagt cgagatcccc gccacggttg atgagagctt tgttgtaggt ggaccagttg     120
gtgattttga acttttgctt tgccacggaa cggtctgcgt tgtcgggaag atgcgtgatc     180
tgatccttca actcagcaaa agttcgattt attcaacaaa gccgccgtcc cgtcaagtca     240
gcgtaatgct ctgccagtgt tacaaccaat taaccaattc tgattagaaa aactcatcga     300
gcatcaaatg aaactgcaat ttattcatat caggattatc aataccatat ttttgaaaaa     360
gccgtttctg taatgaagga gaaaactcac cgaggcagtt ccataggatg caagatcct      420 ggtatcggtc tgcgattccg actcgtccaa catcaataca acctattaat ttcccctcgt     480
```

-continued

```
caaaaataag gttatcaagt gagaaatcac catgagtgac gactgaatcc ggtgagaatg        540
gcaaaagttt atgcatttct ttccagactt gttcaacagg ccagccatta cgctcgtcat        600
caaaatcact cgcatcaacc aaaccgttat tcattcgtga ttgcgcctga gcagacgaa         660 atacgcgatc gctgttaaaa ggacaattac aaacaggaat cgaatgcaac cggcgcagga        720
acactgccag cgcatcaaca atattttcac ctgaatcagg atattcttct aatacctgga        780
atgctgtttt tccggggatc gcagtggtga gtaaccatgc atcatcagga gtacggataa        840
aatgcttgat ggtcggaaga ggcataaaatt ccgtcagcca gtttagtctg accatctcat       900
ctgtaacatc attggcaacg ctacctttgc catgtttcag aaacaactct ggcgcatcgg        960
gcttcccata caatcgatag attgtcgcac ctgattgccc gacattatcg cgagcccatt       1020
tatacccata taaatcagca tccatgttgg aatttaatcg cggcctcgag caagacgttt       1080
cccgttgaat atggctcata acacccctg tattactgtt tatgtaagca gacagttta        1140 ttgttcatga tgatatattt ttatcttgtg caatgtaaca tcagagattt tgagacacaa       1200
cgtggctttc ccccccccc ctatgcggtg tgaaataccg cacagatgcg taaggagaaa        1260
ataccgcatc aggacgcgcc ctgtagcggc gcattaagcg cggcgggtgt ggtggttacg       1320
cgcagcgtga cgctacactt gccagcgccc tagcgcccgc tcctttcgct ttcttccctt       1380
cctttctcgc cacgttcgcc atgcataatg tgcctgtcaa atggacgaag cagggattct       1440 gcaaaccta tgctactccg tcaagccgtc aattgtctga ttcgttacca attatgacaa       1500
cttgacggct acatcattca cttttcttc acaaccggca cggaactcgc tcgggctggc       1560
cccggtgcat tttttaaata cccgcgagaa atagagttga tcgtcaaaac caacattgcg       1620
accgacggtg gcgataggca tccgggtggt gctcaaaagc agcttcgcct ggctgatacg       1680
ttggtcctcg cgccagctta agacgctaat ccctaactgc tggcggaaaa gatgtgacag       1740
acgcgacggc gacaagcaaa catgctgtgc gacgctggcg atatcaaaat tgctgtctgc       1800
caggtgatcg ctgatgtact gacaagcctc gcgtacccga ttatccatcg gtggatggag       1860
cgactcgtta atcgcttcca tgcgccgcag taacaattgc tcaagcagat ttatcgccag       1920
cagctccgaa tagcgccctt ccccttgccc ggcgttaatg atttgcccaa acaggtcgct       1980
gaaatgcggc tggtgcgctt catccgggcg aaagaacccc gtattggcaa atattgacgg       2040
ccagttaagc cattcatgcc agtaggcgcg cggacgaaag taaacccact ggtgatacca       2100
ttcgcgagcc tccggatgac gaccgtagtg atgaatctct cctggcggga acagcaaaat       2160
atcacccggt cggcaaacaa attctcgtcc ctgattttc accacccct gaccgcgaat        2220 ggtgagattg agaatataac ctttcattcc cagcggtcgg tcgataaaaa aatcgagata       2280
accgttggcc tcaatcggcg ttaaacccgc caccagatgg gcattaaacg agtatcccgg       2340
cagcagggga tcattttgcg cttcagccat acttttcata ctcccgccat tcagagaaga       2400
aaccaattgt ccatattgca tcagacattg ccgtcactgc gtcttttact ggctcttctc       2460
gctaaccaaa ccggtaaccc cgcttattaa aagcattctg taacaaagcg ggaccaaagc       2520
catgacaaaa acgcgtaaca aaagtgtcta taatcacggc agaaaagtcc acattgatta       2580
tttgcacggc gtcacacttt gctatgccat agcattttta tccataagat tagcggatcc       2640
tacctgacgc ttttatcgc aactctctac tgtttctcca tacccgtttt tttgggctag       2700
aaataatttt gttaacttt aagaaggaga tataaccatg ataacttctg ctcttcatcg       2760
tgcggccgac tgggctaaat ctgtgttctc ttcggcggcg ctgggtgatc ctcgccgtac       2820
```

-continued

```
tgcccgcttg gttaacgtcg ccgcccaatt ggcaaaatat tctggtaaat caataaccat    2880
ctcatcagag ggtagtaaag ccgcccagga aggcgcttac cgatttatcc gcaatcccaa    2940
cgtttctgcc gaggcgatca gaaaggctgg cgccatgcaa acagtcaagt tggctcagga    3000
gtttcccgaa ctgctggcca ttgaggacac cacctctttg agttatcgcc accaggtcgc    3060
cgaagagctt ggcaagctgg gctctattca ggataaatcc cgcggatggt gggttcactc    3120
cgttctcttg ctcgaggcca ccacattccg caccgtagga ttactgcatc aggagtggtg    3180
gatgcgcccg gatgaccctg ccgatgcgga tgaaaggag agtggcaaat ggctggcagc    3240
ggccgcaact agccggttac gcatgggcag catgatgagc aacgtgattg cggtctgtga    3300
ccgcgaagcc gatattcatg cttatctgca ggacaaactg gcgcataacg agcgcttcgt    3360
ggtgcgctcc aagcacccac gcaaggacgt agagtctggg ttgtatctgt acgaccatct    3420
gaagaaccaa ccggagttgg gtggctatca gatcagcatt ccgcaaaagg gcgtggtgga    3480
taaacgcggt aaacgtaaaa atcgaccagc ccgcaaggcg agcttgagcc tgcgcagtgg    3540
gcgcatcacg ctaaaacagg ggaatatcac gctcaacgcg gtgctggccg aggagattaa    3600
cccgcccaag ggtgagaccc cgttgaaatg gttgttgctg accagcgaac cggtcgagtc    3660
gctagcccaa gccttgcgcg tcatcgacat ttatacccat cgctggcgga tcgaggagtt    3720
ccataaggca tggaaaaccg gagcaggagc cgagaggcaa cgcatggagg agccggataa    3780
tctggagcgg atggtctcga tcctctcgtt tgttgcggtc aggctgttac agctcagaga    3840
aagcttcacg ccgccgcaag cactcagggc gcaaggctg ctaaaggaag cggaacacgt    3900
agaaagccag tccgcagaaa cggtgctgac cccggatgaa tgtcagctac tgggctatct    3960
ggacaaggga aaacgcaagc gcaaagagaa agcaggtagc ttgcagtggg cttacatggc    4020
gatagctaga ctgggcggtt ttatggacag caagcgaacc ggaattgcca gctggggcgc    4080
cctctggtaa ggttgggaag ccctgcaaag taaactggat ggcttttctg ccgccaagga    4140
tctgatggcg caggggatca agatctgatc cgggctttcc ccgtcaagct ctaaatcggg    4200
ggctcgactg tctcttatac acatcttgag tgagtgagaa cctgcattaa tgaatcgggt    4260
accgagctcg aattacttca ctgacaccct catcagtgcc aacatagtaa gccagtatac    4320
actccgctag cgctgatgtc cggcggtgct tttgccgtta cgcaccaccc cgtcagtagc    4380
tgaacaggag ggacagctga tagaaacaga agccactgga gcacctcaaa aacaccatca    4440
tacactaaat cagtaagttg gcagcatcac ccgacgcact ttgcgccgaa taaatacctg    4500
tgacggaaga tcacttcgca gaataaataa atcctggtgt ccctgttgat accgggaagc    4560
cctgggccaa cttttggcga aaatgagacg ttgatcggca cgtaagaggt tccaactttc    4620
accataatga aataagatca ctaccgggcg tattttttga gttatcgaga ttttcaggag    4680
ctaaggaagc taaaatggag aaaaaaatca ctggatatac caccgttgat atatcccaat    4740
ggcatcgtaa agaacatttt gaggcatttc agtcagttgc tcaatgtacc tataaccaga    4800
ccgttcagct ggatattacg gcctttttaa agaccgtaaa gaaaaataag cacaagtttt    4860
atccggcctt tattcacatt cttgcccgcc tgatgaatgc tcatccggaa ttccgtatgg    4920
caatgaaaga cggtgagctg gtgatatggg atagtgttca cccttgttac accgttttcc    4980
atgagcaaac tgaaacgttt tcatcgctct ggagtgaata ccacgacgat ttccggcagt    5040
ttctacacat atattcgcaa gatgtggcgt gttacggtga aaacctggcc tatttcccta    5100
aagggtttat tgagaatatg ttttttcgtct cagccaatcc ctgggtgagt ttcaccagtt    5160
ttgatttaaa cgtggccaat atggacaact tcttcgcccc cgttttcacc atgggcaaat    5220
```

```
attatacgca aggcgacaag gtgctgatgc cgctggcgat tcaggttcat catgccgtct    5280
gtgatggctt ccatgtcggc agaatgctta atgaattaca acagtactgc gatgagtggc    5340
agggcggggc gtaatttttt taaggcagtt attggtgccc ttaaacgcct ggtgctacgc    5400
ctgaataatt gataataagc ggatgaatgg cagaaattcg aaagcaaatt cgacccggtc    5460
gtcggttcag gcagggtcg ttaaatagcc gcttatgtct attgctggtt taccggttta    5520
ttgactaccg gaagcagtgt gaccgtgtgc ttctcaaatg cctgaggcca gtttgctcag    5580
gctctccccg tggaggtaat aattgacgat atgatcattt attctgcctc ccagagcctg    5640
ataaaaacgg ttagcgcttc gttaatacag atgtaggtgt tccacagggt agccagcagc    5700
atcctgcgat gcagatccgg aacataatgg tgcagggcgc ttgtttcggc gtgggtatgg    5760
tggcaggccc cgtggccggg ggactgttgg gcgctgccgg cacctgtcct acgagttgca    5820
tgataaagaa gacagtcata agtgcggcga cgaaattcag atctgatcaa gagacagctg    5880
tcgacgtcag gtggcacttt tcggggaaat gtgcgcggaa cccctatttg tttattttc     5940 taaatacatt caaatatgta tccgctcatg agacaataac cctgataaat gcttcaataa    6000
tattgaaaaa ggaagagtat gagtattcaa catttccgtg tcgcccttat tcccttttt     6060 gcggcatttt gccttcctgt ttttgctcac ccagaaacgc tggtgaaagt aaaagatgct    6120
gaagatcagt tgggtgcacg agtgggttac atcgaactgg atctcaacag cggtaagatc    6180
cttgagagtt ttcgccccga gaacgttttt ccaatgatga gcacttttaa agttctgcta    6240
tgtggcgcgg tattatcccg tattgacgcc gggcaagagc aactcggtcg ccgcatacac    6300
tattctcaga atgacttggt tgagtactca ccagtcacag aaaagcatct tacggatggc    6360
atgacagtaa gagaattatg cagtgctgcc ataaccatga gtgataacac tgcggccaac    6420
ttacttctga caacgatcgg aggaccgaag gagctaaccg cttttttgca acatggggg     6480 gatcatgtaa ctcgccttga tcgttgggaa ccggagctga atgaagccat accaaacgac    6540
gagcgtgaca ccacgatgcc tgtagcaatg gcaacaacgt tgcgcaaact attaactggc    6600
gaactactta ctctagcttc ccggcaacaa ttaatagact ggatggaggc ggataaagtt    6660
gcaggaccac ttctgcgctc ggcccttccg gctggctggt ttattgctga taaatctgga    6720
gccggtgagc gtgggtctcg cggtatcatt gcagcactgg ggccagatgg taagccctcc    6780
cgtatcgtag ttatctacac gacggggagt caggcaacta tggatgaacg aaatagacag    6840
atcgctgaga taggtgcctc actgattaag cattggtaac tgtcagacca gtttactca     6900 tatatacttt agattgattt aaaacttcat ttttaattta aaaggatcta ggtgaagatc    6960 cttttttgata atctcatgac caaaatccct aacgtgagt tttcgttcca ctgagcgtca    7020
gaccccgtag aaaagatcaa aggatcttct tgagatcctt ttttctgcg cgtaatctgc     7080 tgcttgcaaa caaaaaaacc accgctacca gcggtggttt gtttgccgga tcaagagcta    7140
ccaactcttt ttccgaaggt aactggcttc agcagagcgc agataccaaa tactgtcctt    7200
ctagtgtagc cgtagttagg ccaccacttc aagaactctg tagcaccgcc tacatacctc    7260
gctctgctaa tcctgttacc agtggctgct gccagtggcg ataagtcgtg tcttaccggg    7320
ttggactcaa gacgatagtt accggataag gcgcagcggt cgggctgaac ggggggttcg    7380
tgcacacagc ccagcttgga gcgaacgacc tacaccgaac tgagatacct acagcgtgag    7440
ctatgagaaa gcgccacgct tcccgaaggg agaaaggcgg acaggtatcc ggtaagcggc    7500
agggtcggaa caggagagcg cacgagggag cttccagggg gaaacgcctg gtatctttat    7560
```

```
agtcctgtcg ggtttcgcca cctctgactt gagcgtcgat ttttgtgatg ctcgtcaggg    7620
gggcggagcc tatggaaaaa cgccagcaac gcggcctttt tacggttcct ggccttttgc    7680
tggccttttg ctcacatgtt ctttcctgcg ttatcccctg attctgtgga taaccgtatt    7740
accgcctttg agtgagctga taccgctcgc cgcagccgaa cgaccgagcg cagcgagtca    7800
gtgagcgagg aagc                                                      7814
```

<210> SEQ ID NO 10
<211> LENGTH: 9265
<212> TYPE: DNA
<213> ORGANISM: Artificial Sequence
<220> FEATURE:
<223> OTHER INFORMATION: Description of Artificial Sequence: Pgt8

<400> SEQUENCE: 10

```
ctaagaaacc attattatca tgacattaac ctataaaaat aggcgtatca cgaggccctt      60
tcgtcttcaa gggtcgctca ctgcccgctt tccagtcggg aaacctgtcg tgccagctgc     120
attaatgaat cggccaacgc gcggggagag gcggtttgcg tattgggcgc cagggtggtt     180
tttcttttca ccagtgagac gggcaacagc tgattgccct tcaccgcctg gccctgagag     240
agttgcagca agcggtccac gctggtttgc cccagcaggc gaaaatcctg tttgatggtg     300 ttgacggcg ggatataaca tgagctgtct tcggtatcgt cgtatcccac taccgagata     360
tccgcaccaa cgcgcagccc ggactcggta atggcgcgca ttgcgcccag cgccatctga     420
tcgttggcaa ccagcatcgc agtgggaacg atgccctcat tcagcatttg catggtttgt     480
tgaaaaccgg acatggcact ccagtcgcct tcccgttccg ctatcggctg aatttgattg     540
cgagtgagat atttatgcca gccagccaga cgcagacgcg ccgagacaga acttaatggg     600
cccgctaaca gcgcgatttg ctggtgaccc aatgcgacca gatgctccac gcccagtcgc     660
gtaccgtctt catgggagaa aataatactg ttgatgggtg tctggtcaga gacatcaaga     720
aataacgccg gaacattagt gcaggcagct tccacagcaa tggcatcctg gtcatccagc     780
ggatagttaa tgatcagccc actgacgcgt tgcgcgagaa gattgtgcac cgccgcttta     840
caggcttcga cgccgcttcg ttctaccatc gacaccacca cgctggcacc cagttgatcg     900
gcgcgagatt taatcgccgc gacaatttgc gacggcgcgt gcagggccag actggaggtg     960
gcaacgccaa tcagcaacga ctgtttgccc gccagttgtt gtgccacgcg gttgggaatg    1020
taattcagct ccgccatcgc cgcttccact ttttcccgcg ttttcgcaga aacgtggctg    1080
gcctggttca ccacgcggga aacggtctga taagagacac cggcatactc tgcgacatcg    1140
tataacgtta ctggtttcac attcaccacc ctgaattgac tctcttccgg gcgctatcat    1200
gccataccgc gaaaggtttt gcaccattcg atggtgtcgg cagcgttggg tcctggccac    1260
gggtgcgcat gatcgtgctc ctgtcgttga ggacccggct agagtcgcaa cgcaattaat    1320
gtgagttagc tcactcatta ggcaccccag gctttacact ttatgcttcc ggctcgtatg    1380
ttgtgtggaa ttgtgagcgg ataacaattt cacacaggaa acagggtac cctgcttgca    1440 aacaaaaaaa ccaccgctac cagcggtggt ttgtttgccg gatcaagagc taccaactct    1500
ttttccgaag gtaactggct tcagcagagc gcagatacca aatactgtcc ttctagtgta    1560
gccgtagtta ggccaccact tcaagaactc tgtagcaccg cctacatacc tcgctctgct    1620
aatcctgtta ccagtggctg ctgccagtgg cgataagtcg tgtcttaccg ggttggactc    1680
aagacgatag ttaccggata aggcgcagcg gtcgggctga acggggggtt cgtgcacaca    1740
gcccagcttg gagcgaacga cctacaccga actgagatac ctacagcgtg agctatgaga    1800
```

-continued

```
aagcgccacg cttcccgaag ggagaaaggc ggacaggtat ccggtaagcg gcagggtcgg     1860
aacaggagag cgcacgaggg agcttccagg gggaaacgcc tggtatcttt atagtcctgt     1920
cgggtttcgc cacctctgac ttgagcgtcg attttttgtga tgctcgtcag ggggcggag     1980 cctatggaaa aacgccagca acgcggcctt tttacggttc ctggcctttt gctggccttt     2040
tgctcacatg ttctttcctg cgttatcccc tgattctgtg ataaccgta ttaccgcctt     2100 tgagtgagct gataccgctc gccgcagccg aacgaccgag cgcagcgagt cagtgagcga     2160
ggaagcggaa gagcgcctga tgcggtattt tctccttacg catctgtgcg gtatttcaca     2220
ccgcatatgg tgcactctca gtacaatctg ctctgatgcc gcatagttaa gccagtatac     2280
actccgctat cgctacgtga ctgggtcatg gctgcgcccc gacacccgcc aacacccgct     2340
gacgcgccct gacgggcttg tctgctcccg gcatccgctt acagacaagc tgtgaccgtc     2400
tccgggagct gcatgtgtca gaggttttca ccgtcatcac cgaaacgcgc gaggcagctg     2460
cggtaaagct catcagcgtg gtcgtgaagc gattcacaga tgtctgcctg ttcatccgcg     2520
tccagctcgt tgagtttctc cagaagcgtt aatgtctggc ttctgataaa gcgggccatg     2580
ttaagggcgg ttttttcctg tttggtcact gatgcctccg tgtaaggggg aattctgttc     2640 atggggtaa tgataccgat gaacgagag aggatgctca cgatacgggt tactgatgat     2700
gaacatgccc ggttactgga acgttgtgag ggtaaacaac tggcggtatg gatgcggcgg     2760
gaccagagaa aaatcactca gggtcaatgc cagcgcttcg ttaatacaga tgtaggtgtt     2820
ccacagggta gccagcagca tcctgcgatg cagatccgga acataatggt gcagggcgct     2880
gacttccgcg tttccagact ttacgaaaca cggaaaccga agaccattca tgttgttgct     2940
caggtcgcag acgttttgca gcagcagtcg cttcacgttc gctcgcgtat cggtgattca     3000
ttctgctaac cagtaaggca accccgccag cctagatcct tttagcttta tgcttgtaaa     3060
ccgttttgtg aaaaaatttt taaaataaaa aggggaccct ctagggtccc caattaatta     3120
gtaatataat ctattaaagg tcattcaaaa ggtcatccac cggatccgag ctcgaattgt     3180
aagaggttcc aactttcacc ataatgaaat aagatcacta ccgggcgtat ttttttgagtt     3240 atcgagattt tcaggagcta aggaagctaa aatggagaaa aaaatcactg gatataccac     3300
cgttgatata tcccaatggc atcgtaaaga acatttttgag gcatttcagt cagttgctca     3360
atgtacctat aaccagaccg ttcagctgga tattacggcc ttttttaaaga ccgtaaagaa     3420 aaataagcac aagtttttatc cggcctttat tcacattctt gcccgcctga tgaatgctca     3480
tccggaattc cgtatggcaa tgaaagacgg tgagctggtg atatgggata gtgttcaccc     3540
ttgttacacc gttttccatg agcaaactga acgttttca tcgctctgga gtgaatacca     3600
cgacgatttc cggcagtttc tacacatata ttcgcaagat gtggcgtgtt acggtgaaaa     3660
cctggcctat ttccctaaag ggtttattga gaatatgttt ttcgtctcag ccaatccctg     3720
ggtgagtttc accagttttg atttaaacgt ggccaatatg gacaacttct tcgcccccgt     3780
tttcaccatg ggcaaatatt atacgcaagg cgacaaggtg ctgatgccgc tggcgattca     3840
ggttcatcat gccgtctgtg atggcttcca tgtcggcaga atgcttaatg aattacaaca     3900
gtactgcgat gagtggcagg gcggggcgta atttttttaa ggcagttatt ggtgccctta     3960
aacgcctggt gctacgcctg aataattgat aataagcgga tgaatggcag aaattcgaaa     4020
gcaaattcga cccggtcgtc ggttcagggc agggtcgtta aatagccgct tatgtctatt     4080
gctggtttac cggtttattg actaccggaa gcagtgtgac cgtgtgcttc tcaaatgcct     4140
```

```
gaggccagtt tgctcaggct ctccccgtgg aggtaataat tgacgatatg atcatttatt    4200
ctgcctccca gagcctgata aaaacggtta gcgcttcgtt aatacagatg taggtgttcc    4260
acagggtagc cagcagcatc ctgcgatgca gatccggaac ataatggtgc agggcgcttg    4320
tttcggcgtg ggtatggtgg caggccccgt ggccggggga ctgttgggcg ctgccggcac    4380
ctgtcctacg agttgcatga taaagaagac agtcataagt gcggcgacga aattcagatc    4440
tgatcaagag acagctgtcg acgtcaggtg gcacttttcg gggaaatgtg cgcggaaccc    4500
ctatttgttt attttttctaa atacattcaa atatgtatcc gctcatgaga caataaccct    4560
gataaatgct tcaataatat tgaaaaagga agagtatgag tattcaacat ttccgtgtcg    4620
cccttattcc cttttttgcg gcattttgcc ttcctgtttt tgctcaccca gaaacgctgg    4680
tgaaagtaaa agatgctgaa gatcagttgg gtgcacgagg gagcttccag ggggaaacgc    4740
ctggtatctt tatagtcctg tcgggtttcg ccacctctga cttgagcgtc gattttttgtg    4800
atgctcgtca ggggggcgga gcctatggaa aaacgccagc aacgcggcct ttttacggtt    4860
cctggccttt tgctggcctt tgctcacat gttctttcct gcgttatccc ctgattctgt    4920
ggataaccgt attaccgcct ttgagtgagc tgataccgct cgccgcagcc gaacgaccga    4980
gcgcagcgag tcagtgagcg aggaagcgac agctgtctct tgatcagatc tcatgcaagc    5040
ttcagctcac tcactcaaga tgtgtataag agacagtcga gatccccgcc acggttgatg    5100
agagctttgt tgtaggtgga ccagttggtg attttgaact tttgctttgc cacggaacgg    5160
tctgcgttgt cgggaagatg cgtgatctga tccttcaact cagcaaaagt tcgatttatt    5220
caacaaagcc gccgtcccgt caagtcagcg taatgctctg ccagtgttac aaccaattaa    5280
ccaattctga ttagaaaaac tcatcgagca tcaaatgaaa ctgcaattta ttcatatcag    5340
gattatcaat accatatttt tgaaaaagcc gtttctgtaa tgaaggagaa aactcaccga    5400
ggcagttcca taggatggca agatcctggt atcggtctgc gattccgact cgtccaacat    5460
caatacaacc tattaatttc ccctcgtcaa aaataaggtt atcaagtgag aaatcaccat    5520
gagtgacgac tgaatccggt gagaatggca aaagtttatg catttctttc cagacttgtt    5580
caacaggcca gccattacgc tcgtcatcaa aatcactcgc atcaaccaaa ccgttattca    5640
ttcgtgattg cgcctgagcg agacgaaata cgcgatcgct gttaaaagga caattacaaa    5700
caggaatcga atgcaaccgg cgcaggaaca ctgccagcgc atcaacaata ttttcacctg    5760
aatcaggata ttcttctaat acctggaatg ctgttttttcc ggggatcgca gtggtgagta    5820
accatgcatc atcaggagta cggataaaat gcttgatggt cggaagaggc ataaattccg    5880
tcagccagtt tagtctgacc atctcatctg taacatcatt ggcaacgcta cctttgccat    5940
gtttcagaaa caactctggc gcatcgggct tcccatacaa tcgatagatt gtcgcacctg    6000
attgcccgac attatcgcga gcccatttat acccatataa atcagcatcc atgttggaat    6060
ttaatcgcgg cctcgagcaa gacgtttccc gttgaatatg gctcataaca ccccttgtat    6120
tactgtttat gtaagcagac agttttattg ttcatgatga tatattttta tcttgtgcaa    6180
tgtaacatca gagattttga gacacaacgt ggctttcccc ccccccccta tgcggtgtga    6240
aataccgcac agatgcgtaa ggagaaaata ccgcatcagg acgcgccctg tagcggcgca    6300
ttaagcgcgg cgggtgtggt ggttacgcgc agcgtgacgc tacacttgcc agcgccctag    6360
cgcccgctcc tttcgctttc ttcccttcct ttctcgccac gttcgccatg cataatgtgc    6420
ctgtcaaatg gacgaagcag ggattctgca aaccctatgc tactccgtca agccgtcaat    6480
tgtctgattc gttaccaatt atgacaactt gacggctaca tcattcactt tttcttcaca    6540
```

-continued

```
accggcacgg aactcgctcg ggctggcccc ggtgcatttt ttaaatacccc gcgagaaata    6600 gagttgatcg tcaaaaccaa cattgcgacc gacggtggcg ataggcatcc gggtggtgct    6660
caaaagcagc ttcgcctggc tgatacgttg gtcctcgcgc cagcttaaga cgctaatccc    6720
taactgctgg cggaaaagat gtgacagacg cgacggcgac aagcaaacat gctgtgcgac    6780
gctggcgata tcaaaattgc tgtctgccag gtgatcgctg atgtactgac aagcctcgcg    6840
tacccgatta tccatcggtg gatggagcga ctcgttaatc gcttccatgc gccgcagtaa    6900
caattgctca agcagattta tcgccagcag ctccgaatag cgcccttccc cttgcccggc    6960
gttaatgatt tgcccaaaca ggtcgctgaa atgcggctgg tgcgcttcat ccgggcgaaa    7020 gaacccccgta ttggcaaata ttgacggcca gttaagccat tcatgccagt aggcgcgcgg    7080
acgaaagtaa acccactggt gataccattc gcgagcctcc ggatgacgac cgtagtgatg    7140
aatctctcct ggcgggaaca gcaaaatatc cccggtcgg caaacaaatt ctcgtccctg    7200 attttttcacc acccctgac cgcgaatggt gagattgaga atataacctt tcattcccag    7260
cggtcggtcg ataaaaaaat cgagataacc gttggcctca atcggcgtta aacccgccac    7320
cagatgggca ttaaacgagt atcccggcag caggggatca ttttgcgctt cagccatact    7380
tttcatactc ccgccattca gagaagaaac caattgtcca tattgcatca gacattgccg    7440
tcactgcgtc ttttactggc tcttctcgct aaccaaaccg gtaaccccgc ttattaaaag    7500
cattctgtaa caaagcggga ccaaagccat gacaaaaacg cgtaacaaaa gtgtctataa    7560
tcacggcaga aaagtccaca ttgattattt gcacggcgtc acactttgct atgccatagc    7620
atttttatcc ataagattag cggatcctac ctgacgcttt ttatcgcaac tctctactgt    7680
ttctccatac ccgttttttt gggctagaaa taattttgtt taactttaag aaggagatat    7740
aaccatgata acttctgctc ttcatcgtgc ggccgactgg gctaaatctg tgttctcttc    7800
ggcggcgctg gtgatcctc gccgtactgc ccgcttggtt aacgtcgccg cccaattggc    7860
aaaatattct ggtaaatcaa taaccatctc atcagagggt agtaaagccg cccaggaagg    7920
cgcttaccga tttatccgca atcccaacgt ttctgccgag gcgatcagaa aggctggcgc    7980
catgcaaaca gtcaagttgg ctcaggagtt tcccgaactg ctggccattg aggacaccac    8040
ctctttgagt tatcgccacc aggtcgccga agagcttggc aagctgggct ctattcagga    8100
taaatcccgc ggatggtggg ttcactccgt tctcttgctc gaggccacca cattccgcac    8160
cgtaggatta ctgcatcagg agtggtggat gcgcccggat gaccctgccg atgcggatga    8220
aaaggagagt ggcaaatggc tggcagcggc cgcaactagc cggttacgca tgggcagcat    8280
gatgagcaac gtgattgcgg tctgtgaccg cgaagccgat attcatgctt atctgcagga    8340
caaactggcg cataacgagc gcttcgtggt gcgctccaag cacccacgca aggacgtaga    8400 gtctggggttg tatctgtacg accatctgaa gaaccaaccg gagttgggtg ctatcagat    8460 cagcattccg caaaagggcg tggtggataa acgcggtaaa cgtaaaaatc gaccagcccg    8520
caaggcgagc ttgagcctgc gcagtgggcg catcacgcta aaacagggga atatcacgct    8580
caacgcggtg ctggccgagg agattaaccc gcccaagggt gagacccgt tgaaatggtt    8640 gttgctgacc agcgaaccgg tcgagtcgct agcccaagcc ttgcgcgtca tcgacattta    8700
tacccatcgc tggcggatcg aggagttcca taaggcatga aaaaccggag caggagccga    8760
gaggcaacgc atgaggagc cggataatct ggagcggatg gtctcgatcc tctcgtttgt    8820
tgcggtcagg ctgttacagc tcagagaaag cttcacgccg ccgcaagcac tcagggcgca    8880
```

```
                                                                -continued agggctgcta aaggaagcgg aacacgtaga aagccagtcc gcagaaacgg tgctgacccc    8940
ggatgaatgt cagctactgg gctatctgga caagggaaaa cgcaagcgca aagagaaagc    9000
aggtagcttg cagtgggctt acatggcgat agctagactg ggcggtttta tggacagcaa    9060
gcgaaccgga attgccagct ggggcgccct ctggtaaggt tgggaagccc tgcaaagtaa    9120
actggatggc tttcttgccg ccaaggatct gatggcgcag gggatcaaga tctgatccgg    9180
gctttccccg tcaagctcta aatcgggggc tcgactgtct cttatacaca tcttgagtga    9240
gtgagaacct gcattaatga atcgg                                          9265
```

US 7,067,644 B2

DOUBLE TRANSPOSITION METHODS FOR MANIPULATING NUCLEIC ACIDS

CROSS-REFERENCE TO RELATED APPLICATIONS

This application claims the benefit of U.S. Provisional Patent application No. 60/251,482, filed Dec. 5, 2000, which application is incorporated by reference herein as if set forth in its entirety.

STATEMENT REGARDING FEDERALLY SPONSORED RESEARCH OR DEVELOPMENT

This invention was made with United States government support awarded by the National Institutes of Health, Grant No. GM50692. The United States has certain rights in this invention.

BACKGROUND OF THE INVENTION

Manipulation of nucleic acids and proteins is an important aspect of modern molecular biology. In particular, the science of combinatorial genetics has advanced in recent years as it has become apparent that proteins having altered structure and function can be engineered by swapping large or small portions of the amino acid sequence with other related or unrelated amino acid sequences. Using this approach, it is also possible to engineer novel proteins that bring together in a single molecule the structures and functions of diverse molecules. Such manipulations are most readily undertaken at the nucleic acid level. The nucleic acids thus produced can be transcribed to produce fusion RNAs and translated either in vitro or in vivo using known methods and the recombinant proteins thus produced can be isolated. Other manipulations, such as inserting polynucleotides of interest into a chromosome, deleting sections of a chromosome, or cloning sections of a chromosome are also of interest. Moreover, various approaches are known for shuffling gene pieces and selecting or screening for products having one or more desired activities or properties. Examples of such technologies include U.S. Pat. Nos. 5,605,793, 5,830,721, and 6,132,970. A number of companies including Maxygen, Diversa, Applied Molecular Evolution, and Genencor International among others specialize in directed molecular evolution. See Pollack, A., "Selling Evolution in Ways Darwin Never Imagined," New York Times, page B1, Oct. 28, 2000.

Recently, non-transposition based methods for generating large libraries of randomly fused genes have been reported. Ostermeir and co-workers first described a method termed ITCHY that involves the incremental truncation of two genes by use of ExoIII nuclease followed by S1 nuclease treatment, polymerization, and ligation of fragments to form random fusions (Ostermeier et al., 1999; Lutz et al., 2000). A second method has also been reported that utilizes random cleavage of DNA followed by a series of digestion and ligation reactions to create random fusions. This technique, called SHIPREC, also has features that increase the amount of useful fusions if both proteins have similar length and domain organization (Seiber et al., 2001). Existing methods for gene shuffling and chromosome manipulation are complex and can exhibit a bias for or against particular recombination sites and sequences. Thus, the art continues to develop more sophisticated manipulations.

Various aspects of an in vitro transposition system that employs sequences from, and sequences derived from, the Tn5 transposon are described in U.S. Pat. Nos. 5,925,545, 5,948,622, and 5,965,443, each of which is incorporated by reference herein as if set forth in its entirety. International publication Number WO 00/17343, also incorporated herein by reference as if set forth herein in its entirety, discloses a system for introducing into cells synaptic complexes that comprise a Tn5 transposase and a polynucleotide having flanking sequences that operably interact with the transposase to form a synaptic complex.

Even though these known systems for Tn5-based in vitro transposition are effective and very useful, they do not provide sufficient manipulative control to meet the technological goals noted above.

Efforts are also underway to define so-called minimal bacterial genomes for growth under defined conditions and, similarly, to identify genes essential for growth under defined conditions. Determining the content required for a minimal bacterial genome is of intense interest. One approach is to assemble the theoretical minimal genome in silico by comparing a variety of different microbial genomes. Alternatively, the smallest genome amongst existing genomes (mycoplasma) can be analyzed by mutagenesis. $E.coli$ K12 is a preferred bacterium, because of its simplicity in handling, and its short generation time. It is desirable to try to generate a minimal or significantly reduced $E.coli$ K12 genome, which may shorten the already short doubling time in rich media.

Recently developed transposon-based approaches involve inserting a transposon into a gene to (1) knockout or disrupt a gene function or (2) introduce a lethal mutation that cannot be observed in an essential gene. These methods essentially catalogue transposition into non-essential genes. It is assumed that any gene that contains no transposon insert is essential.

An important alternative approach involves affirmatively identifying essential genes in libraries of cells, where the cells contain transposons having selectively regulated outwardly-facing promoters inserted upstream from an essential gene. While the cells of interest are not viable on media that cannot activate a transposon promoter, expression is restored by selectively activating either or both of the transposon promoters. Unfortunately, only a few of the transposon inserts in a library will insert into the promoter region of an essential gene.

BRIEF SUMMARY OF THE INVENTION

In a first aspect, the invention is summarized in that a transposable polynucleotide is suitable for use in methods for manipulating nucleic acids to create libraries of cells that contain transposed nucleic acid when the polynucleotide comprises two or more inverted repeat sequence pairs ("transposase-interacting sequences") arranged as disclosed herein, where each pair has a distinct and separable ability to interact with a distinct transposase enzyme. The pairs can be provided in a nested fashion such that both members of one pair are flanked by both members of the second pair. In a related aspect, it is not essential to provide two complete pairs of transposase-interacting sequences in a single transposon, nor to introduce all of the transposase-interacting sequences by transposition. Rather, as will become more apparent below, a first member of one pair can separately be provided directly on the substrate DNA for use in a second of two transposition events with a second member of the pair, the second member being introduced during a first of two transposition events. By providing and arranging selectable markers, origins of replication, and/or other nucleotide sequences of interest on the transposable polynucleotide, one can direct sequential transposition processes to achieve the desired manipulated nucleic acids.

In a related aspect, the invention is a transposable polynucleotide having transposase-interacting sequences and additional sequences arranged as disclosed elsewhere herein. The nature of the arrangement dictates the uses to which the transposable polynucleotides can be put.

In yet another aspect, the invention is summarized in that the transposable polynucleotides are introduced into host cells as disclosed to produce libraries of cells that achieve the objects of the invention. Using selection and screening methods, cells that have undergone desired transpositions can be obtained. In certain embodiments, the host cells transcribe and translate double transposition products produced entirely in vitro. In other embodiments, a synaptic complex formed in vitro between a first transposase and a transposable polynucleotide of the invention is introduced into a host cell whereupon the transposable polynucleotide is transposed into the host cell chromosome. This first transposition is followed, upon induction of a second transposase, by a second round of transposition in vivo to yield chromosomal insertions or deletions or cloned products excised from the host cell chromosome.

In another aspect, the invention is summarized in that a host cell contains an extrachromosomal circular polynucleotide that comprises first and second polynucleotide fusion portions, each polynucleotide fusion portion comprising a pair of segments from a pair of sequences that can encode a fusion RNA that can be translated to produce a fusion polypeptide, the members of the pair flanking a pair of transposase-interacting sequences each having a distinct and separable ability to interact with one of a pair of transposase enzymes, the pair of transposase-interacting sequences defining a junction between the two segments. In certain embodiments, the junction has a nucleic acid sequence that permits transcription and translation of both fusion segments across the junction.

In yet another aspect, the present invention is summarized in that a host cell contains a chromosome deleted in length relative to a wild type chromosome and comprising at the deletion site in place of the excised material, a pair of transposase-interacting sequences each having a distinct and separable ability to interact with one of a pair of transposase enzymes. In certain embodiments, the host cell further contains a self-replicating nucleic acid molecule that itself comprises the deleted portion of the host cell chromosome. In other embodiments, the host cell chromosome further comprises at the deletion site a segment of pre-selected nucleic acid between the pair of transposase-interacting sequences.

Still another aspect of the invention is summarized in that the transposase-interacting sequences are inverted repeats provided in inverted pairs on the polynucleotide for transposition. The two kinds of transposase-interacting sequences can be separate from one another, can be abutted end to end, or can overlap when it is particularly desirable to minimize the size of such sequence elements. As is detailed below, the transposase-interacting sequences can be engineered to ensure an open reading frame in either or both polarity, as desired.

It is an object of the invention to provide a system for manipulating nucleic acids in vitro and in vivo.

It is another object of the invention to generate a library of random fusions between two polynucleotide or polypeptide sequences, preferably between sequences that, respectively, encode and define peptides or proteins of interest.

It is a feature of the invention that the system employs two pairs of transposase-interacting sequences each interacting with a distinct transposase.

It is an advantage of the invention that transpositions occur without regard to the sequences of the nucleic acids into which the transposable elements transpose.

It is another advantage of the invention that large libraries (e.g., >$10^7$ individuals) having a high level of variability can be produced.

Other objects, features and advantages will become apparent upon consideration of the following detailed description taken in conjunction with the accompanying drawings.

DETAILED DESCRIPTION OF THE INVENTION

Figure 1:
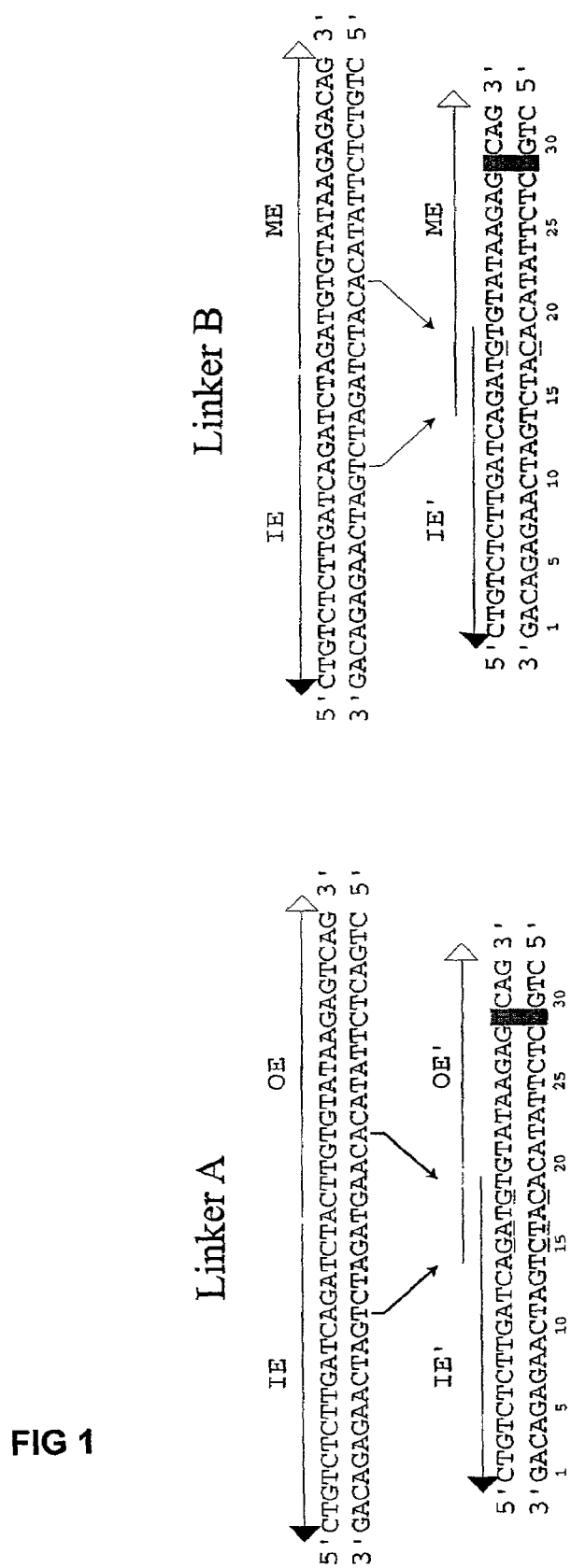
FIG. 1 depicts a pair of preferred arrangements of full-length and interleaved (compressed) transposase-binding sequences that face in opposite directions. The full-length version of the IE/OE linker (Linker A) is accorded SEQ ID NO: 1, and the corresponding compressed version of the IE/OE linker is accorded SEQ ID NO: 2. Likewise, the full-length version of the IE/ME linker (Linker B) is accorded SEQ ID NO: 3, and the corresponding compressed version of the LE/ME linker is accorded SEQ ID NO: 4.

Mutant Tn5 transposase enzymes can preferentially bind to and interact with distinct inverted repeat sequences. The end preference of a mutant transposase can be characterized either (1) by the in vivo transposition frequency observed when it is used in a system in which the target polynucleotide is flanked with particular termini, or (2) by the ratio of the in vivo transposition frequencies observed when it is used in a pair of systems in which the target polynucleotide is flanked with the termini, respectively. In vitro transposition frequency characterization is also possible.

The constructs and methods of the invention all employ two pairs of inverted repeat sequences ("transposase-interacting sequences") that bind to and interact with a pair of transposase enzymes to facilitate directed double transposition as detailed below. The transposases are referred to generally herein as transposase 1(Tnp1) and transposase 2(Tnp2). There are no preordained requirements for the transposase-interacting sequences except that the combination of Tnp1 and the sequences that preferentially bind to and interact with it have a distinct and separable activity from the combination of Tnp2 and its preferential binding sequences.

By way of example, the Tn5 transposon includes inside end sequences (IE) and outside end sequences (OE). A transposase that preferentially binds to and interacts with OE, but not IE, is known and disclosed in incorporated U.S. Pat. No. 5,965,443. The hyperactive transposase there disclosed includes a mutation at position 54 and a mutation at position 372 that confer upon the Tn5 transposase a greater avidity for Tn5 outside end repeat sequences than wild type Tn5 transposase. A preferred embodiment of that transposase includes a lysine at position 54 and a proline at position 372. A most preferred embodiment of that transposase also includes an alanine residue at position 56. The preferred transposase of U.S. Pat. No. 5,965,443 is referred to as Tnp EK/LP. All embodiments of the transposase disclosed in the incorporated patent are useful in the present invention. In the examples that follow, this transposase is represented as Tnp2.

Further incorporated U.S. Pat. No. 5,925,545 discloses that a Tnp EK/LP-transposase-catalyzed in vitro transposition frequency at least as high as that of wild type OE is achieved if the termini include bases ATA at positions 10, 11, and 12, respectively, as well as the nucleotides in common between wild type OE and IE (e.g., at positions 1–3, 5–9, 13, 14, 16, and optionally 19). The nucleotides at positions 4, 15, 17, and 18 can correspond to the nucleotides found at those positions in either wild type OE or wild type IE. It is noted that the transposition frequency can be further enhanced over that of wild type OE if the nucleotide at position 4 is a T. The so-called "mosaic end sequences" ("ME") of U.S. Pat. No. 5,925,545 can be advantageously used in the present invention instead of wild-type OE sequences. Where "ME" sequences are used in the patent application, it is understood that ME and wild type OE sequences can be used, although use of ME yields a higher transposition frequency. Accordingly, Tnp2 can also be referred to as Tnp-OE or Tnp-ME. It is noted that, in the presence of Tnp EK/LP (Tnp2), a transposon having one ME and one OE transposes at higher frequency than one having a pair of OE termini. Transposons having ME—ME termini seem to transpose at a still slightly higher frequency.

On the other hand, a second class of hyperactive Tn5 transposase mutants exhibits a dramatic preference for Tn5 inside end sequences, and in some cases, methylated inside ends ($IE^{ME}$), rather than for outside ends (OE), which are unmethylated because they lack a methylation site. The members of this class of Tn5 transposase mutants differ from wild-type Tn5 transposase protein at least at amino acid position 58 or position 372. In a preferred version, the second hyperactive Tn5 transposase mutant differs from wild-type in that it includes a cysteine at amino acid position 8, a valine at amino acid position 58, a lysine at amino acid position 344, and a glutamine at amino acid position 372. This transposase having four differences from wild type Tn5 transposase is referred to as Tnp sC7v2.0 and is used in the examples that follow, where it is represented as Tnp1 or Tnp-IE.

The aforementioned transposase enzymes having distinct and separable abilities to interact with distinct transposase-interacting sequences are preferred transposases for use in the methods of the invention. However, as long as one coordinates the relative positions of the transposase-interacting sequence pairs with the sequence (order) of providing the appropriate transposase, there is no requirement that either one of the transposases corresponds to transposase Tnp1 or Tnp2 as shown in the Figures. It is advantageous that the transposase enzymes have a hyperactive transposition efficiency relative to wild-type Tn5 transposase. Particularly when screening for transposition events, it is desirable for every cell to have undergone a transposition event. Accordingly, as a guideline, at least a 1000 fold activity increase relative to wild-type Tn5 transposase is considered to be preferred. The Tnp sC7v2.0 IE-specific enzyme described above is about 1000 fold more active than wild-type Tn5 transposase. The Tnp EK/LP is at least again about 10–100 fold more hyperactive than Tnp sC7v2.0. Mutant derivatives of these enzymes having still higher transposition activities while retaining their indicated specificities would be advantageously employed in the methods.

One can practice the method by providing the pairs of transposase-interacting sequences on a transposon in a nested manner such that the outer pair is employed to introduce the transposon into a target DNA. As an alternative, one member of a first pair of transposase-interacting sequences can be provided on the target while the second is provided in a proper orientation on the transposon, flanked by the second pair. When the transposon is subsequently introduced into the target, the first and second members of the first pair of transposase-interacting sequences are then positioned for subsequent transposition in the presence of a suitable transposase enzyme.

It is also possible, but less preferred, to practice the methods of the invention using a single transposase enzyme with pairs of the corresponding end sequence arranged in inverted back-to-back positions. In this approach, one can rely upon the screening and selection methods to yield only the transposition products of interest. However, the method is less preferred because it cedes some measure of control over the transposition processes themselves.

The methods of the invention are described below and are conceptually related in that each takes advantage first of one transposase/end sequence set to accomplish a first transposition event and then, second, of a second transposase/end sequence set to accomplish the second transposition event. By carefully engineering the placement of various components on the transposable element in each case, one can produce fusion RNAs, fusion proteins, chromosomal deletions, chromosomal insertions, or cloned chromosomal segments. The precise structures of the pairs of transposase-interacting sequences are described below. At this juncture, it is important only to note when considering the following disclosure that, in this application, Tnp1 preferentially binds to and interacts with the end sequences shown schematically as black triangles while Tnp2 preferentially binds to and interacts with the end sequences shown as white triangles. The triangle points signify the inverted orientations of the members of each pair.

In the methods of the present invention, Tnp1 and Tnp2 are separately and sequentially provided to donor and target DNA molecules to promote directed evolution by two sequential transposition events. The result of the various methods disclosed depends upon the components provided on the transposed polynucleotides. Conceptually, it makes no difference whether Tnp1 or Tnp2 is used first, as long as the ends are provided in an orientation that directs the two transposition events to occur in the desired order.

There is some flexibility permitted in designing the sequences of the transposase-interacting sequences without appreciably reducing the OE- (or ME-) or IE-specific binding of the transposases. The incorporated US patents describe which bases of the end sequences can be altered without unacceptably reducing the hyperactivity of the appropriate transposase. The ability to modify the end sequences can be advantageously exploited to produce a linker, such as the linker shown as compressed Linker A in FIG. 1, wherein the OE-related sequence (OE') and the IE-related sequence (IE') overlap with one another in a linker that is shorter than would be achieved by abutting the OE and IE sequences to one another. Linker A was designed by combining the IE and OE sequences. The overlap region does not match exactly the sequence of either IE or OE, hence the designations IE' and OE'. The 19 base pairs read from the top left are the IE sequence with position 18 changed from C to G (IE'). The 19 base pairs read from the bottom right match the OE sequence with positions 17 and 18 (linker positions 16 and 15) changed from AG to TC (OE'). As an alternative, compressed Linker B in FIG. 1 depicts a similar overlapped dual function linker engineered to respond to IE and ME, the mosaic ends mentioned above. Compressed Linker B differs from compressed Linker A only at position 29, as shown.

The full-length version of an IE/OE linker of FIG. 1 is accorded SEQ ID NO:1. The compressed version of an IE/OE linker of FIG. 1 (Linker A) is accorded SEQ ID NO:2. The full-length version of an IE/ME linker of FIG. 1 is accorded SEQ ID NO:3. The compressed version of an IE/ME linker of FIG. 1 (Linker B) is accorded SEQ ID NO:4.

The ability to translate gene B—gene A and gene A—gene B fusion proteins depends upon the presence in the linker region of an open reading frame in one or both directions. By carefully designing the linkers, one can allow both fusion products to be translated from start to finish or can ensure that only one fusion orientation is functional. The linkers can also be engineered to ensure that at least one reading frame is free of stop codons. This attribute ensures that combinatorial fusion proteins are translated through the transposition site. It may be preferable to design the linker so that only one reading frame is open so that all functional fusions have the same amino acids inserted at the transposition junction. It is also possible to recover functional fusion proteins in the method by altering either or both of the gene A and gene B starting target sequences such that no functional protein can be produced without two sequential transposition events, as described.

When producing gene fusion products according to the invention, the length of the linker is also important. If the length of the linker is a multiple of three and the linker contains only one open reading frame, the fusion point between the protein segments will have a constant amino acid sequence. A second consideration concerns the number of inserted amino acids resulting from the linker. It can be desirable to minimize the disruption to the natural proteins by using as short a linker as possible. However, this can present challenges because it is difficult to overlap the linkers without introducing changes to the OE (or ME) and IE sequences that are detrimental to transposition frequency. The compressed linkers of FIG. 1 are likely to be the shortest possible linkers that employ these binding sequences. As noted above, Linker A has an IE end and an OE end; Linker B has an IE end and an ME end (see FIG. 1).

If no overlap is provided in the linker (and none is required in this or any disclosed embodiment), a thirty-nine nucleotide long linker would include a complete OE (or ME) sequence, a complete IE sequence, and a single nucleotide therebetween to bring the length of the linker to a multiple of three. These considerations are of no concern when using the invention for manipulations other than gene fusions. Indeed, in the subsequent embodiments, the linkers can be overlapping, abutted or non-overlapping unless another aspect of the method dictates a separation between mismatched transposase-interacting sequences.

Figure 2:
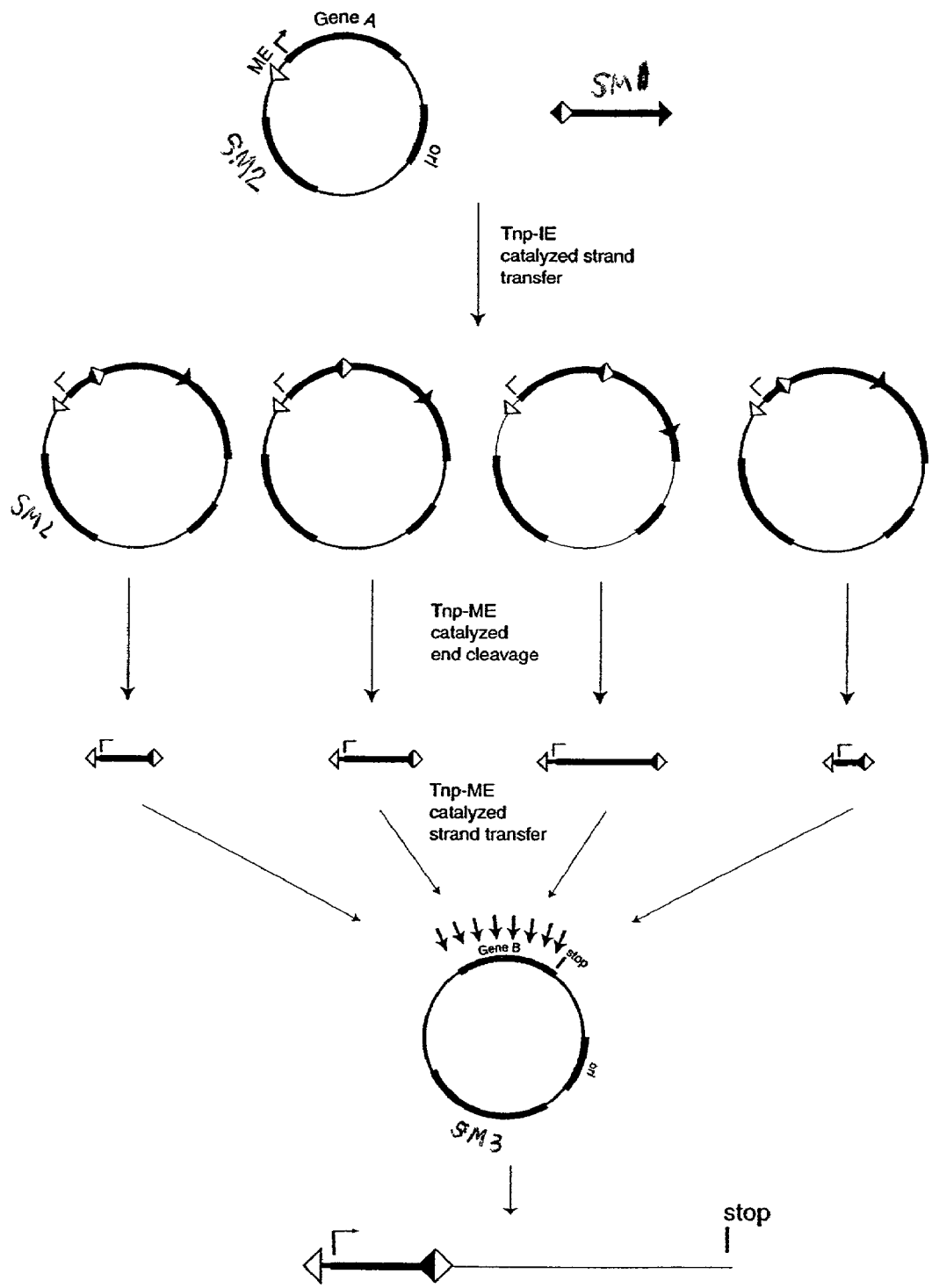
FIG. 2 depicts a first approach to a method for producing a gene fusion library for obtaining directed gene and protein evolution products. In the first approach, a first transposase binds to and interacts with first transposase-interacting sequences in a donor polynucleotide (shown schematically as black triangles) whereupon the newly created transposon is transposed into a first target nucleic acid molecule that contains an appropriately-oriented transposase-interacting sequence to yield a set of first transposition products. Then, a second transposase binds to and interacts with the second transposase-interacting sequences, now both resident in the members of the set of first transposition products (shown schematically as white triangles), whereupon the donor portions of the first products are transposed into a second target nucleic acid molecule. The resulting nucleic acid molecule comprises a fusion sequence having a junction portion that includes a pair of distinct transposase-interacting sequences. It will be understood that only a few exemplary transposition products are shown, but that, in fact, the library of transposition products produced reflects the combinatorial variety resulting from the sequential transposition processes.
Figure 3:
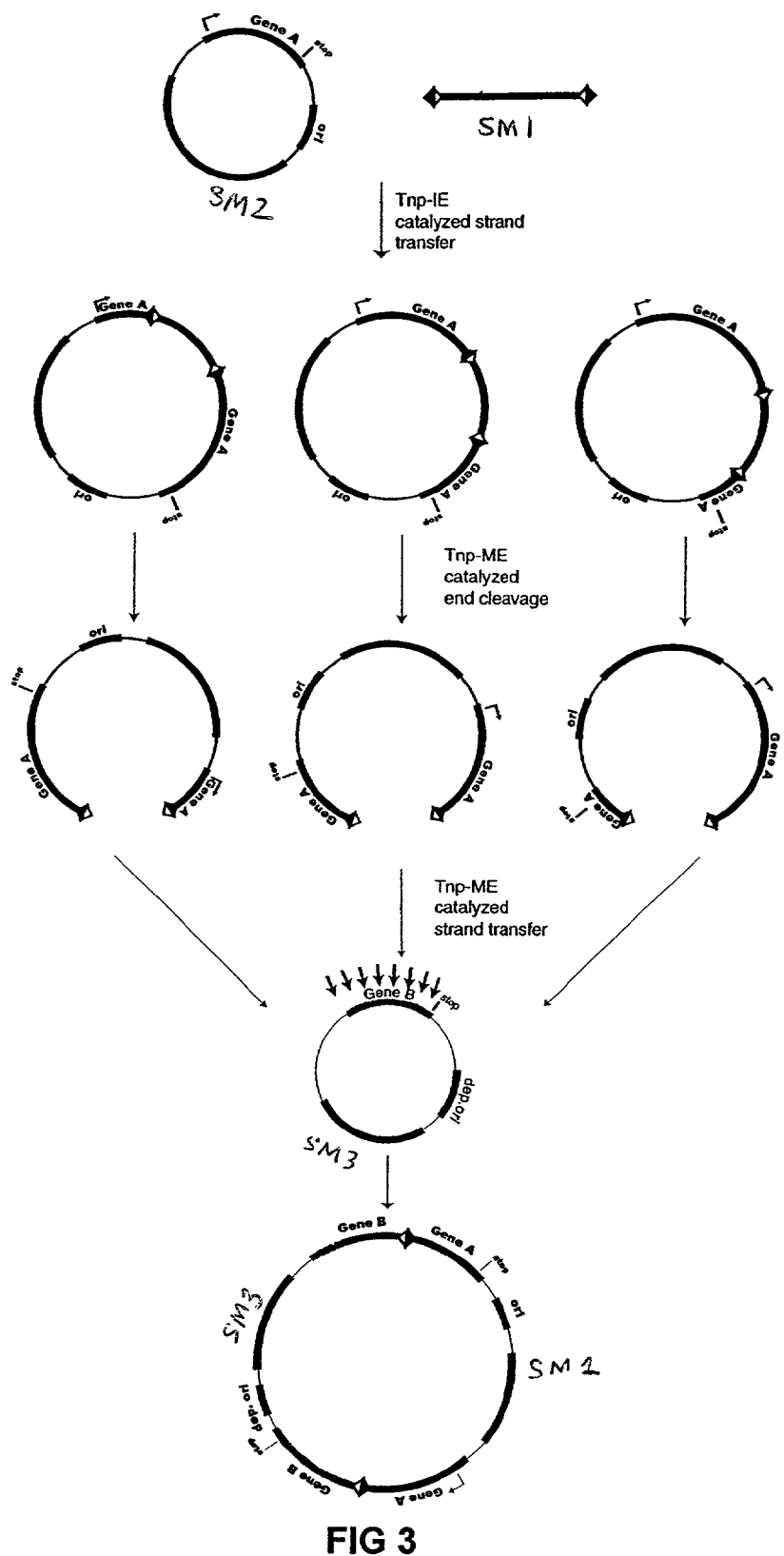
FIG. 3 depicts a second approach to a method for producing a gene fusion library for obtaining directed gene and protein evolution products. In the second approach, a first transposase binds to and interacts with first transposase-interacting sequences in a donor polynucleotide (shown schematically as black triangles) whereupon the newly created transposon is transposed into a first target nucleic acid molecule to yield a set of first transposition products. Then, a second transposase binds to and interacts with the second transposase-interacting sequences in the first transposition products (shown schematically as white triangles) whereupon the donor portions of the first products are transposed into a second target nucleic acid molecule. The resulting nucleic acid molecule comprises a pair of fusion sequences, each fusion sequence having a junction portion that includes a pair of distinct transposase-interacting sequences. Again, it will be understood that only a few exemplary transposition products are shown, but that, in fact, the library of transposition products produced reflect the combinatorial variety resulting from the sequential transposition processes.

It is instructive to look first at the simplest embodiments of the invention, namely processes for generating libraries of nucleic acid molecules such as plasmids that contain a pair of fused genes that can encode chimeric proteins as shown in FIGS. 2 and 3. A pair of distinct protein-encoding (or partial protein-encoding) sequences (Gene A and Gene B) are provided on separate molecules. A goal of these methods for forming fusion proteins is to bring together N-terminal portions of one protein-encoding sequence with C-terminal portions of a second protein-encoding sequence, where the library of resulting fusions includes a random set of junction points. The gene portions can be from unrelated or related genes. This can be accomplished in either of two approaches that share a single underlying principle, although the constructs employed differ slightly, as is discussed below. Also, the construct that contains sequences encoding the C-terminal portion of the fusion can optionally further comprise another polynucleotide fused to the sequence that encodes the C-terminus, where the additional polynucleotide encodes a protein that can be directly selected for. This technique not only selects expressed fusion proteins for screening, but also eliminates translated fusions that result in proteins that are poorly expressed or have low solubility (Maxwell et al., 1999). The successful use of a CAT gene for selecting non-homologous gene fusions has previously been reported. (Sieber et al., 2001).

In one approach, depicted in FIG. 2, a transposon that confers resistance to selectable marker SM1 is transposed into a first gene using Tnp1 to produce an initial insert library. Using Tnp2, the products of that library are transposed into a second gene to form fusion proteins. More particularly, each of a pair of genes A and B is provided on a separate construct that also comprises an origin of replication and distinct selectable markers, SM2 and SM3, respectively. Gene A contributes its N-terminal portion, and Gene B contributes its C-terminal portion, to the fusion protein. In this approach, the construct that contains Gene A also includes a single Tnp2 transposase-interacting sequence upstream of the gene's promoter.

The aforementioned Gene A construct is then mixed with a pre-cleaved transposon that includes yet another distinct selectable marker (SM1) flanked at a first end by a first Tnp1-specific transposase-interacting sequence, and at a second end by a transposase-interacting sequence pair having a Tnp2-specific sequence and a second Tnp1-specific sequence, where the Tnp2-specific sequence is between the selective marker and the second Tnp1-specific sequence. In a first transposition reaction between these two nucleic acid molecules in the presence of an amount of Tnp1 effective to catalyze transposition, the transposon inserts into the target construct at random positions, some of which are in Gene A. Reaction products are then transformed into suitable host cells, such as E. Coli cells, under standard transformation conditions. Electroporation is a suitable transformation method. The transformed cells are grown under selective pressure (SM1 and SM2) for cells that contain constructs having the Gene A construct and an integrated transposon. The resulting selected cells constitute the initial library of random linker inserts.

In the presence of an amount of Tnp2 effective to catalyze transposition, DNA from the initial insert library serves in a second transposition reaction as the transposon donor. The initial insert library DNA is mixed with the target Gene B construct and incubated until transposons are cleaved from the initial insert library and then inserted at random locations into the target construct to create the library of random fusion constructs that can encode random fusion proteins having an N-terminal end contributed by Gene A and a C-terminal end contributed by Gene B. The products are transformed into suitable host cells and selected for SM3 and against SM1 and SM2, which indicates the presence of Gene B construct without the Gene A construct or the original transposon of the first reaction. It should be noted that the Tnp2-interacting sequence in half of all inserts in the resulting initial insert library is inverted. Such inserts cannot participate in the second transposition reaction.

As mentioned above, one can alternatively introduce the transposase-interacting sequences entirely by transposition, instead of providing a single Tnp2-interacting sequence on the Gene A construct. In this second approach, two fusions are created. This second approach also employs a pre-cleaved transposon and separate Gene A and Gene B constructs. Neither of the two constructs contains transposase binding sequences at the start of the method, although one of the two constructs contains a conditional origin of replication to prevent improper replication of the dual-origin fusion construct that is formed in the method by joining the two starting constructs. Since some fusion constructs can have two origins, improper replication could result if both starting constructs contain non-conditional origins of replication.

FIG. 3 depicts this second approach. In contrast to the first approach, the orientation of insertion is not important, as the double ends exist on both ends of the transposon. In the first transposition step, parts of genes A and B are transposed to yield a library containing two classes of fusion products, namely (1) the N-terminal end of Gene A fused to the C-terminal end of Gene B and (2) the N-terminal end of Gene B fused to the C-terminal end of Gene A, which can be transcribed and translated to produce fusion RNAs and fusion proteins.

To carry out the first transposition step in this second approach, a pre-cut transposon encoding selectable marker SMI flanked by pairs of transposase-interacting sequences as shown and described is combined with a replication competent circular nucleic acid molecule that contains an origin of replication (which can be a conditional origin of replication such as a π-dependent ori) and a selectable marker as well as a gene sequence (Gene A) that can encode a protein. Gene A should include a transcriptional promoter upstream of the gene and a stop codon at the end of the coding sequence. The two are combined in the presence of a first transposase (Tnp1) that preferentially binds to and interacts with the pair of transposase-interacting sequences shown in black under conditions that promote in vitro transposition.

Plasmids in the library of in vitro transposition reaction products can be introduced into host cells by electroporation and cells that contain a plasmid having a transposon insertion in the protein-encoding gene of interest are obtained by plating the host cells on a medium that selects for resistance to SM1 and SM2. The selection method ensures that no member of the library has received an insertion in either the origin of replication or the selectable marker provided on the plasmid. A short linker segment remains at each fusion junction. The junction point at which the coding sequence of the first protein ends is randomly determined by this first in vitro transposition (strand transfer) reaction. These libraries typically contain a sufficient number of independent survivals ($>10^5$) to encompass all possible insertion sites, as determined by plating of a small dilution of the transformation mixture onto agar plates in the presence of both drugs.

In a second in vitro transposition reaction shown in FIG. 3, DNA from the members of the initial library are mixed in vitro under conditions that favor in vitro transposition with a second plasmid containing an origin of replication, a third selectable marker SM3, and a second gene of interest (gene B optionally with promoter) which is intended to be fused with gene A. The origin of replication can be a conditional origin of replication if the origin of replication used in the first step was not a conditional origin. In this second round of in vitro transposition, plasmids from the first transposition library and the second plasmid are mixed under suitable conditions with the second transposase (Tnp2) which binds to and interacts with the pair of inverted repeats shown in white. In the resulting in vitro transposition, the selectable marker present on the original transposon is lost, as it forms the donor backbone DNA, and the remainder of the library plasmids are the transposable portions transposed into plasmid B. After transformation into a suitable host, those colonies that grow in the presence of SM2 and SM3 contain fusions as shown at the bottom of FIG. 3. The resulting reactions products can be directly transformed into suitable host cells and grown in mixed liquid culture under double drug selection to generate a library of desirable products. Plating of small aliquots from reactions has revealed that the library can contain >$10^7$ independent gene fusions. Alternatively, the reaction products can be subjected to selection of functional fusion products. These fusion polynucleotides can encode fusion RNAs that can be translated to produce fusion polypeptides (also referred to interchangeably herein as proteins). The total size of an individual chimeric protein can vary from zero to the total length of both proteins plus the linker segment. One can analyze the nucleic acid members of a fusion library thus created using standard cleavage and sizing methods to demonstrate the presence of fusion products.

This fusion method can be accomplished with no intermediate transfer into a host cell by relying on a single selection after the second transposition process, although this approach is disfavored because of reduced efficiency and, consequently, reduced library size. Because the transposition products in the first stage do not represent a large percentage of the total DNA, it is instead advantageous to purify the initial products so that the ratio of reactants in the second stage can be controlled to promote efficient formation of the desired products.

It is noted that many microbial selection techniques are known, including without limitation the use of selectable markers and biosynthetic and auxotrophic selections, and any such technique can be employed in the method. Selectable markers are employed in the exemplified embodiments because they are convenient and easily manipulated. A skilled artisan will understand that the selectable marker resistance gene chosen for use at any stage of the methods is not critical and all that is required is that the selection technique be appropriate for the chosen resistance gene. By way of non-limiting example, the marker can confer resistance to kanamycin, chloramphenicol, ampicillin, tetracycline or other drugs.

When manipulating the nucleic acid and cells as described herein, commercially available *E. coli* K-12 DH5 cells (recA) or JM109 cells are suitable, if no conditional origin of replication is in use. In the latter case, cells that supply the protein required for conditional replication (such as TransforMax EC100D pir-116 electrocompetent *E. coli* K12 cells, commercially available from Epicentre, Madison, Wis.) are suitable. For deletion methods any bacterial strain that supports Tn5 transposition, preferably an *E. coli* strain such as MG1655 (ATCC 47076), can be used.

The number of actual transpositional protein fusions is limited both because the correct reading frame is maintained in only 1 of 3 events and also because the transposition insert is oriented properly in only 1 of 2 events in the second reaction. Therefore, a maximum of 1 out of 6 (16.7%) of all transpositional fusions can be true protein fusions. Although this limitation on the number of productive fusion products can be ignored when the library is large, as here, it may be otherwise desirable to screen for functionally productive fusions.

The percentage of functional fusion products is further limited both by stop codons in the linker and by nonessential DNA other than the gene of interest in the construct. The former can be overcome or reduced as needed by modifying the linker sequence as appropriate to eliminate stop codons. While certain such changes could alter or even destroy the transposition reaction efficiency, it is likely that not every change that removed a stop codon would also affect transposition efficiency. The latter can be overcome by careful engineering constructs to ensure that only inserts into the gene of interest can produce productive transposition products that can both replicate and encode proper drug resistance.

Figure 4:
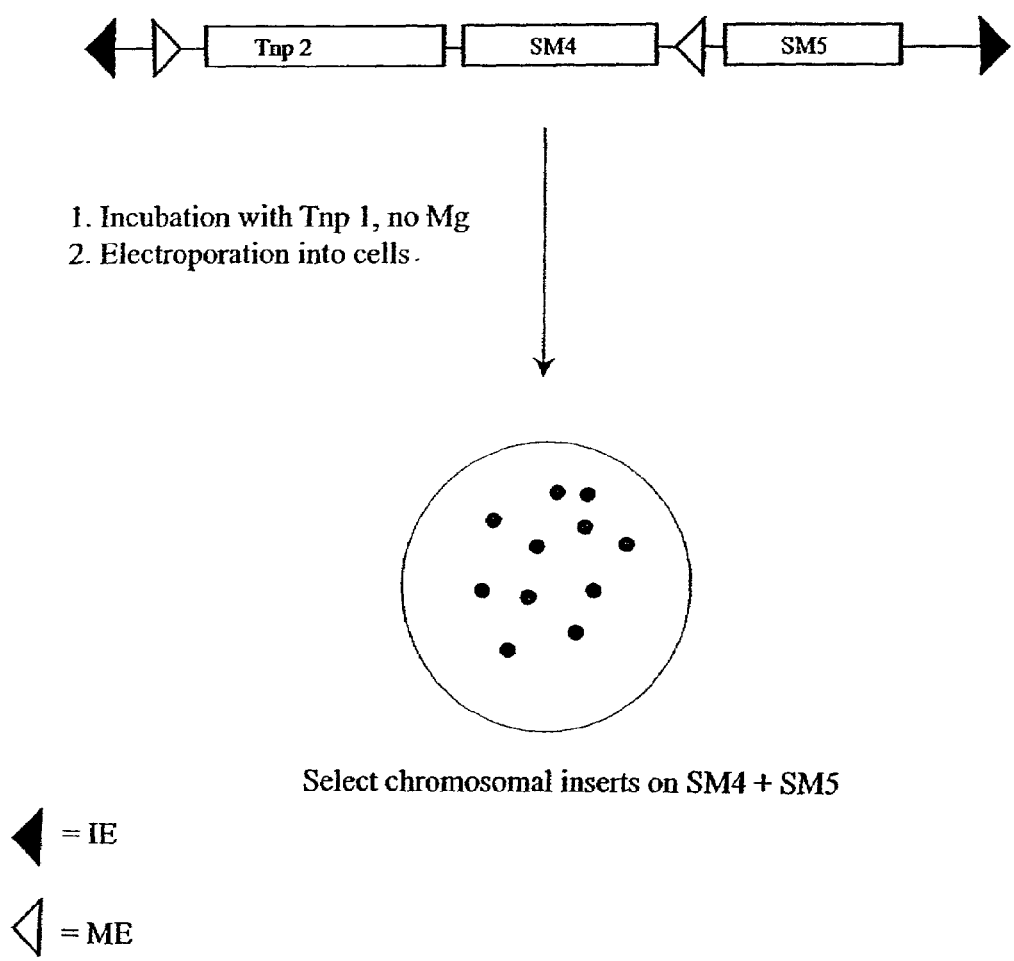
FIG. 4 depicts a first aspect of a construct and method for inserting the construct into a chromosome of bacterial host cell using the method for incorporating a synaptic complex between a transposase enzyme and donor DNA into a host cell chromosome as disclosed in incorporated International patent Application No. WO 00/17343. Other constructs described below can also be inserted into a bacterial host cell chromosome using this same first aspect.

Essentially the same principles apply in the additional methods disclosed below. However, each of the following methods employ as a first step the synaptic complex formation and electroporation method disclosed in incorporated International Patent Application Number WO/00/7343. Briefly, as shown in FIG. 4 a precut transposon containing two pairs of transposase-interacting sequences arranged as disclosed in FIG. 4 is incubated with Tnp1 that binds to and interacts with the pair of black transposase-interacting sequences in the absence of magnesium. The initial incubation step forms a synaptic complex poised for a first transposition event in the presence of a target DNA. Upon introducing the synaptic complex into cells by, e.g., electroporation, the synaptic complex transposes into the bacterial chromosome. After introduction into the host cells, those cells that have incorporated the transposon into their chromosome can be selected by screening for the presence of both SM4 and SM5.

Figure 5:
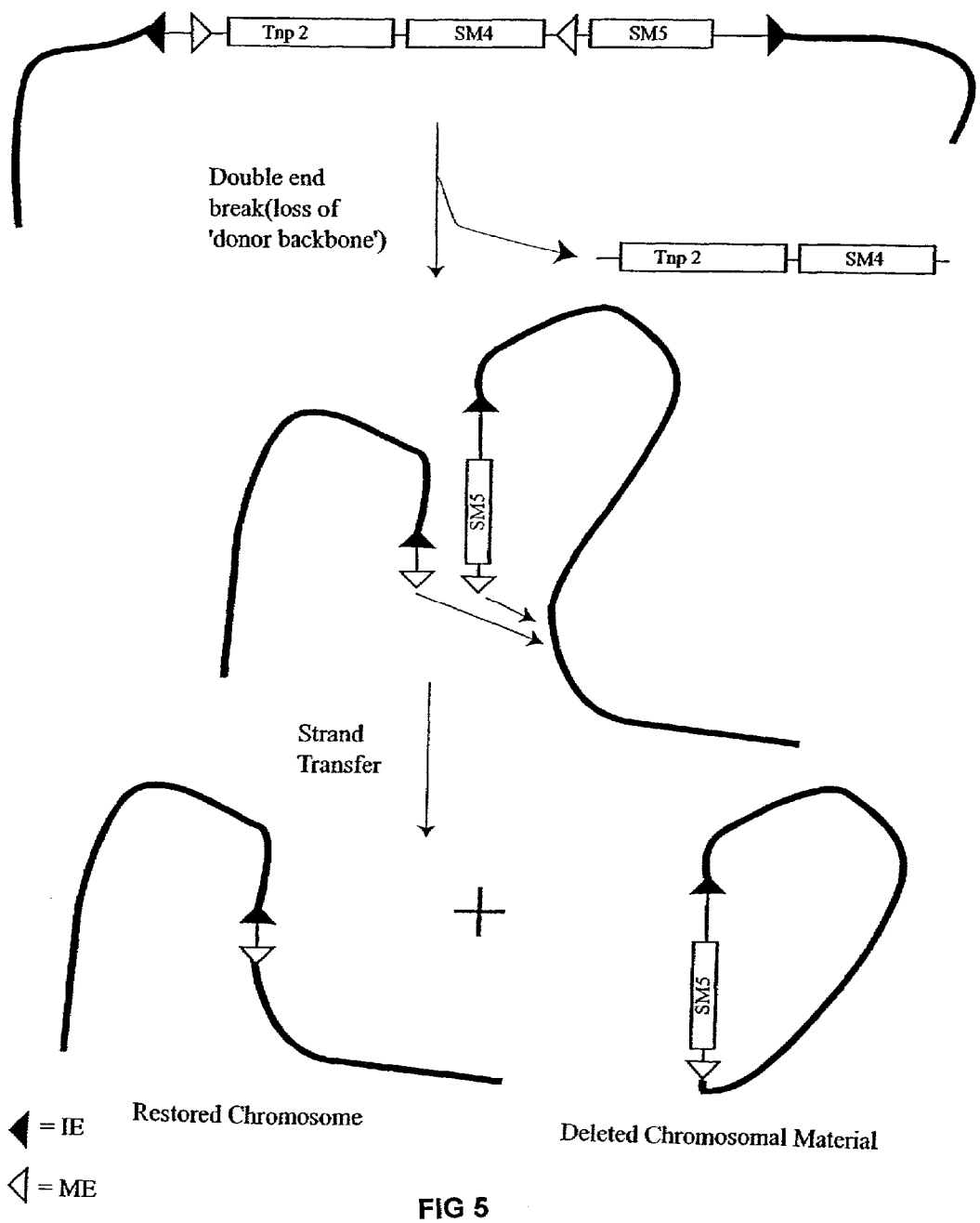
FIG. 5 depicts intrachromosomal in vivo transposition of a construct introduced into the bacterial chromosome as generally shown and described in FIG. 4. This in vivo transposition yields a deleted chromosome carrying a small residual mismatched pair of transposase binding sequences. A second circular product carries a segment of deleted chromosomal material that cannot replicate because it lacks a bacterial origin of replication.

All colonies produced in the first stage of these transposition methods can inducibly encode Tnp2. To induce expression of Tnp2, a colony or set of colonies are inoculated into a selection-free liquid medium containing an inducing agent. The choice of an inducing agent is entirely up to the convenience of the user and has no bearing upon the operation of the invention. A suitable inducing agent would be arabinose, where the arabinose promoter is provided upstream of the transposase-encoding sequence on the transposon. Arabinose is preferred because its promoter is tightly regulated. Upon induction, Tnp2 is synthesized, then binds to and interacts with the white pair of transposase-interacting sequences and a second round of transposition results. At some frequency, the transposition is intrachromosomal and as a result, a portion of the chromosome is deleted and the remaining chromosomal material is recircularized. Accordingly, a somewhat smaller chromosome results. The only evidence of the second transposition event is one residual mismatched pair of end sequences as is shown in FIG. 5.

Figure 6:
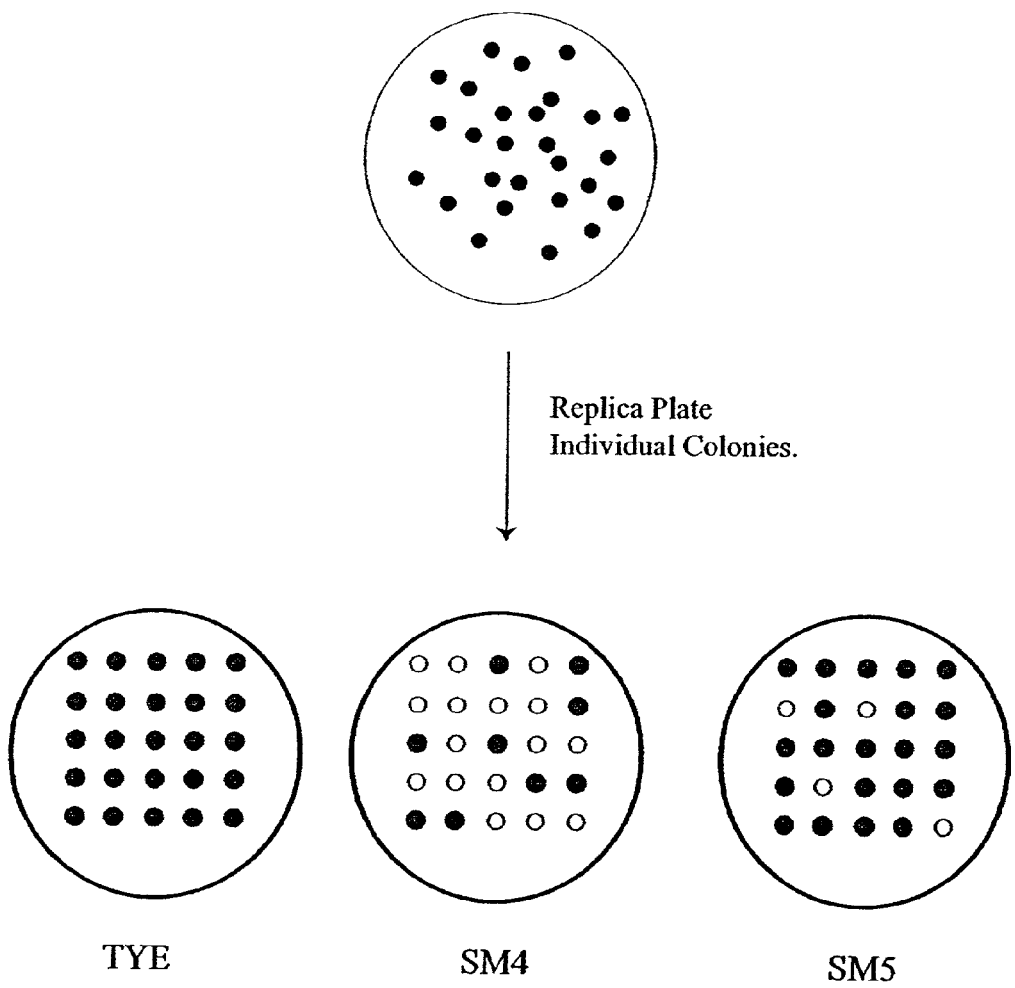
FIG. 6 depicts a screen for deletion products following the double transposition method of FIGS. 4 and 5.

One can readily screen for those colonies that contain a true deletion event. After induction of the second transposase and overnight growth to permit in vivo transposition, the cells are diluted and plated without drug selection (e.g., on TYE plates). Then, individual colonies are replica plated either on permissive medium or on medium containing SM4 or SM5. As shown in FIG. 6, all the colonies will grow on the permissive medium, assuming that none has suffered a deletion in an essential gene. However, only those colonies that are also sensitive to both SM4 and SM5 are in fact deletion mutants.

A similar approach is utilized to permit the excised portion of the chromosome to be replicated and cloned. In this embodiment of the invention, shown in FIG. 7, a simple addition of an origin of replication in the portion of the transposon that is not between the inner (white) pair of transposase-interacting sequences accomplishes this goal. It is important to take due care to ensure that the origin of replication employed is not detrimental or lethal to the host cell. The transposon is introduced into the chromosome as in FIG. 4. Likewise, Tnp2 is induced in precisely the same way. Upon intrachromosomal transposition, however, the excised portion, shown at the bottom right of FIG. 7, contains an origin of replication and can be maintained as an extrachromosomal plasmid.

Figure 8:
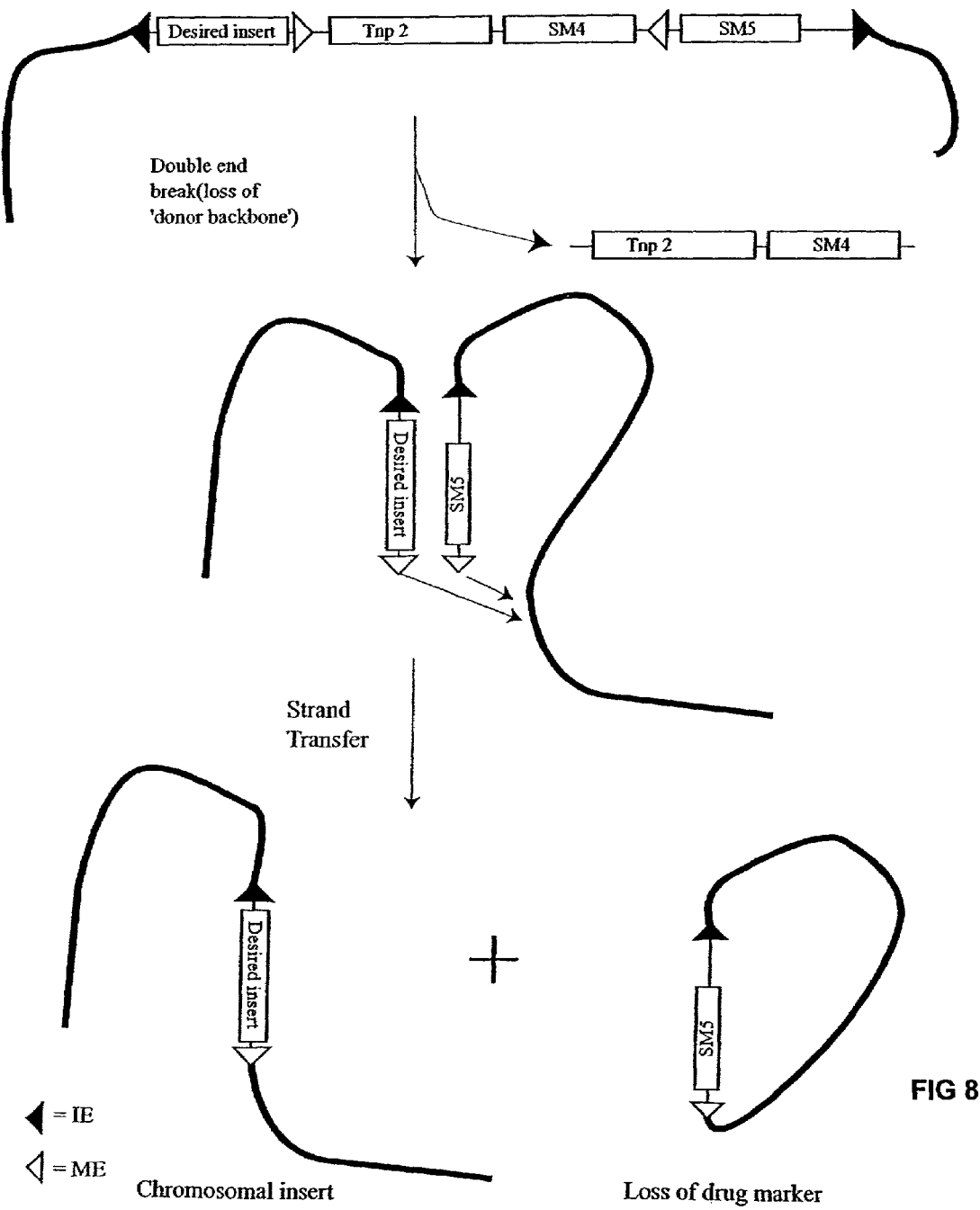
FIG. 8 depicts an intrachromosomal in vivo transposition of a construct introduced into the bacterial chromosome as generally shown and described in FIG. 4. By including in this construct a desired insert, between a mismatched pair of transposase binding sequences, the resulting bacterial chromosome includes the insert at the site of the chromosomal deletion that yields a desired insert added into the bacterial chromosome at the site of the first transposition event.

Finally, relying upon precisely the same principles as the preceding two embodiments, the next embodiment facilitates insertion of a DNA of interest into the chromosome in place of the deleted portion. In this embodiment, shown in FIG. 8, the insert DNA is provided on the transposon outside of the inner (white) pair of transposase-interacting sequences but not on the segment of the transposon that includes SM5. This portion of the transposon remains in the chromosome after the second round of transposition. As is shown in FIG. 8, SM5 is lost with the deleted portion of the chromosome while the desired insert is inserted in place of the deleted portion.

In any of the disclosed embodiments, the products of a first double transposition method can, in fact, act as substrates for a second round of double transposition thereby further increasing the variety of the products. In particular, the chromosomal deletion and gene fusion embodiments are well suited to practicing multiple iterations of the method. By coupling the ability to produce a wide variety of fusion proteins with a known ability to screen for those proteins having desired structures or functions makes the disclosed method of great interest to the pharmaceutical industry, among others. At least the cloning and deletion methods can also be practiced entirely in vitro on non-chromosomal targets (e.g., plasmids).

Figure 7:
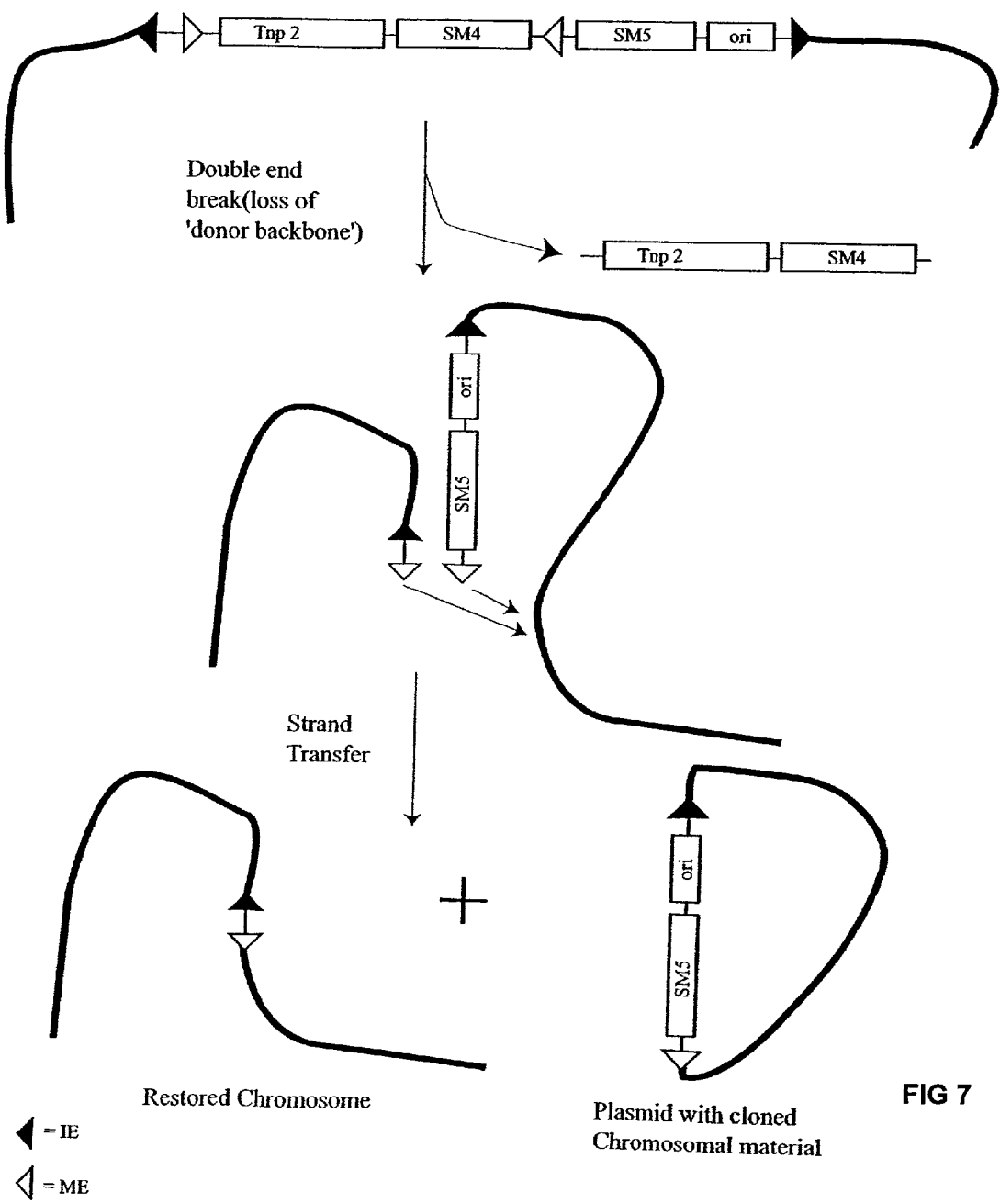
FIG. 7 depicts intrachromosomal in vivo transposition of a construct introduced into the bacterial chromosome as generally shown and described in FIG. 4. By including an origin of replication in this construct, the deleted chromosomal material (as in FIG. 5) can be maintained, amplified, and isolated for further use or study.

To obtain products of the methods shown in FIGS. 7, one can use a regulated origin of replication on the resulting plasmid to provide additional level of selection. To obtain products of the methods shown in FIG. 8, one can merely replica plate the induced cells and select or screen those that have lost or retained the selectable marker or markers of interest, as appropriate for each method.

Direct analysis of the random, non-lethal chromosomal deletion products can reveal the largest deletion that can support growth in particular medium. Moreover, because these deletion products leave behind only a small DNA segment and no selectable markers or transposase coding sequences, the process can be performed recursively, such that the deletion product is used in a subsequent round of insertion or deletion. By repeating this process several times, it is possible to reduce the size of the genome, even to the point of producing a bacterial strain that contains a chromosome having only those genes essential for reproduction.

Additionally, a key requirement in high throughput DNA sequencing is to have a technology in place that will allow a defined primer binding site to be moved next to the region to be sequenced. A single transposition insertion event "randomly" places 2 primer binding sites within a target DNA molecule. In contrast, the double transposition deletion formation system of the invention can advantageously generate multiple constructs from a single transposon insert thereby "moving" a single primer binding site to a plurality of target DNA locations. An embodiment of this methodology is described in the following paragraphs.

A transposon is constructed with distinct pairs of nested transpose-interacting sequences in inverted orientation relative to each another (as described elsewhere herein). For example, if the outer pair are IE sequences and the inner pair are ME sequences, the IE sequences with an appropriate Tnp1 are used to generate initial insertions and the ME sequences with an appropriate Tnp2 are used to generate adjoining deletions as described. Appropriately placed inside the element are suitable selective markers and primer binding sites.

The transposon is inserted at random using the IE specific transposase in vitro into a target cloned DNA, such as a BAC clone. The transposon inserted target clone is transformed into cells and independent transformants are isolated and grown up. DNA sequencing is performed using two primers off of the two ends of the transposon inserts.

From each insert, or from selected inserts, multiple adjacent deletions are generated using Tnp2. This can be accomplished either in vivo (requiring prior transformation and then in vivo synthesis of transposase) or in vitro followed by transformation. A suitable primer is then employed to sequence across the deletion end points into adjacent sequences. Each insert and deletion can also be physically mapped using appropriate restriction digests if desired.

Although the methods of the invention are exemplified using transposable polynucleotides having two transposase-interacting sequence pairs that interact with two transposases, this is not intended to be a limitation on the invention, since one can engineer any greater number of transposase-interacting sequences into a transposable polynucleotide, as long as a transposase having a distinct activity can be used in combination with each such sequence pair.

EXAMPLE 1

Restoration of Chloramphenicol Acetyl Transferase (CAT) from N- and C-Terminally-Truncated Genes Plasmid Vectors Plasmids were maintained in *E. coli* K12 (DH5α), except plasmids that contained a π-dependent origin of replication which were maintained in EC100 pir-116 cells. Plasmids were purified using a quiafilter midi kit (Quiagen). Pre-cleaved transposons were released from the appropriate purified plasmids by cleavage with a restriction enzyme and were then purified by electrophoresis and gel extraction using the quiaquick gel purification kit (quiagen).

The plasmid vectors for the first approach to gene fusion were as shown in FIG. 2. A first plasmid containing a kanamycin resistance gene flanked by one IE and one IE/OE linker end (Linker A) was constructed using standard techniques from starting plasmid pGT4 (SEQ ID NO:8) which encodes a kanamycin resistance gene flanked by IE sequences. This plasmid was the source of pre-cleaved transposon, which was released from the resulting plasmid by cleavage with PshA1. A second plasmid contained a C-terminally truncated CAT gene fragment encoding the first 171 of 219 amino acids and an upstream promoter next to a transposon-interacting sequence specific for ME, as shown at the top of FIG. 2. The source of the CAT gene fragment was pACYC184 (New England Biolabs). The CAT gene was cloned into a vector between ME sequences. The vector also included an origin of replication and a gene conferring resistance to ampicillin. The 3'-end of the gene and the adjacent ME sequence were deleted from the plasmid by cleavage with AflII and subsequent religation. This plasmid was the target in the first transposition reaction. A comparable approach was taken to generating a third plasmid that contained an N-terminally truncated CAT gene fragment encoding all but the first 38 amino acids. In this case a short PvuII fragment was excised from pACYC184 and then relegated. The third plasmid also included an origin of replication and a gene conferring resistance to tetracycline. This plasmid was the target in the second transposition reaction.

The plasmid vectors for the second approach to gene fusion were as shown in FIG. 3. The source of pre-cleaved transposon substrate for the first transposition reaction was like that of the first approach, except that Linker A (or, in an alternative embodiment, Linker B) was provided in appropriate orientation at both ends of the transposon that confers resistance to kanamycin. The second plasmid contained a full length CAT gene (Gene A), an origin of replication and a gene that confers ampicillin resistance. The third plasmid contained an N-truncated CAT gene (Gene B) and a pi-dependent origin of replication. It will be appreciated that either the second or the third plasmid can be provided with the pi-dependent origin, which is advantageously used in maintaining members of interest in a library. Similarly, it is understood that the genes provided on the plasmids can be full length or partial length, depending upon the nature of the genes and the goal of the particular transposition process.

Gene Fusion Protocol

In all transposition reactions, DNAs were combined with the appropriate Tnp in transposition reaction buffer (0.1 M potassium glutamate, 25 mM Tris acetate, pH 7.5, 10 mM $Mg^{2+}$ acetate, 50 µg/ml bovine serum albumin, 0.5 mM β-mercaptoethanol, 2 mM spermidine, 100 µg/ml tRNA; final concentrations) in a total volume of 20 µl. Tnp1 and Tnp2 were purified using the IMPACT system (New England Biolabs) as described previously (Bhasin et al., 1999).

In the first transposition reaction, pre-cleaved transposon and target plasmid were added to a final concentration of 20 nM each. Tnp1 was added to a final concentration of 200 nM and the reactions were incubated at 37° C. for 3 hours. Products were then subjected to treatment with SDS (0.5%) and heat (68C for 5 minutes) to remove Tnp from transposition products and to increase transformation efficiency (data not shown). Treated reaction products were then dialyzed against water and transformed into electrocompetent E. coli K12 cells (DH5α; efficiency=$8.0 \times 10^8$ cfu/µl plasmid). Cells were grown at 37° C. in 1 ml of Luria-Bertani Medium (LB, Difco) to allow expression of antibiotic resistance genes. The culture was then used to inoculate 50 ml of LB containing appropriate antibiotics and grown at 37° C. for 16 hours. A small aliquot of culture following the initial 1 hour growth was removed and plated onto agar media to estimate library size ($>10^5$).

In the second transposition reaction, purified plasmid DNA from the insert library and the second target plasmid were added to a concentration of 80 nM each. Tnp2 was then added to a concentration of 400 nM. Reactions were allowed to incubate at 37° C. for 1 hour and then treated with SDS and heat, dialyzed, and transformed as above.

In the second approach, the initial insert library was generated by mixing pre-cleaved transposon having Linker A at both of its ends with a target plasmid that contained sequences for the N-terminal truncation of the CAT gene in the presence of Tnp1. The library was transformed into E. coli host cells which were outgrown in 1 ml of LB without drugs for 1 hour and subsequently inoculated into 50 ml LB and allowed to grow overnight in the presence of double antibiotic selection. The insert library was then purified. In the second reaction, plasmid DNA from the insert library was then mixed with the second plasmid that contained that contained sequences for the C-terminal truncation of the CAT gene. Tnp2 was added to cleave N-terminal fragments from the CAT gene in the insert library and insert them randomly into the second target plasmid. The reaction products were then transformed into E. coli host cells and plated on LB agar containing 20 µg/ml chloramphenicol to select for functional CAT fusions.

Although successful, Linker A was inefficient, so Linker B was tested in the same way. Due to the order in which the two plasmids were used, the linker orientation for fused genes was in the opposite direction (ME to IE) to those created by method one.

Gel electrophoresis confirmed that the plasmid fusion libraries of the second approach contained one major band, indicating that the double drug selection efficiently chose the desired products from the second transposition reaction without prior purification. Fusion plasmids were shown to contain a unique EcoRV site from the first target plasmid and a unique ScaI site from the second target plasmid. Double digestion of a single fusion plasmid yielded two linear DNA bands having a combined size equal to that of the fused plasmids (not shown). However, as expected, a smear of DNA bands of varying size was observed when the library was double-digested with EcoRV and ScaI because the size of the two bands in each fusion plasmid is different, given that the two plasmids fuse at random positions in each individual product.

To confirm the presence of the transposon linker sequence and to determine the amino acid sequence of the functional fusions, plasmid DNA from a few chloramphenicol resistant colonies obtained in each approach were purified and sequenced. No matter which approach was taken, functional fusions were obtained. Eight functional fusions (obtained from both approaches) were analyzed. None was a 'perfect' fusion (showing no loss or duplication of amino acids). Seven of the eight included a duplicated CAT fragment, ranging in length from 5 amino acids to 54 amino acids in length. One fusion was formed by a 9 amino acid deletion.

Structural information for the CAT protein used in this study, which originates from transposon Tn9, does not exist. However, X-ray crystallographic structure information is available for the related type III Chloramphenicol Acetyltransferase (CATIII) (Leslie, 1990). A BLAST alignment of the primary amino acid sequences of CAT and CATIII revealed that the two proteins have 46% amino acid identity with only a single gap. This alignment was used to map the location of linker insertion in functional CAT fusions to the CATIII structure. This analysis predicts that, of the sixteen linker-CAT junctions, 15 are inserted in disordered regions, while the remaining junction is predicted to be inserted into a β-sheet one amino acid from the terminus. Although these results come from only one protein fusion example, the analysis strongly suggests that functional fusions are formed when the linker sequence does not insert into a location that interrupts either α-helices or β-sheets.

EXAMPLE 2

Deletions and Identification of Essential Genes

Media. For all experiments we used Luria broth liquid or plates media adjusted with antibiotics if needed as follow: chloramphenicol 20 mg/L, kanamicin 40 mg/L, ampicillin 100 mg/L.

Bacterial strains. E.coli K12 strain MG1655 with a known sequence of chromosomal DNA (Blattner et al. 1997) was used for making deletions. E.coli K12 strain DH5α (Sambrook at al. 1989) was used for DNA manipulations.

Figure 9:
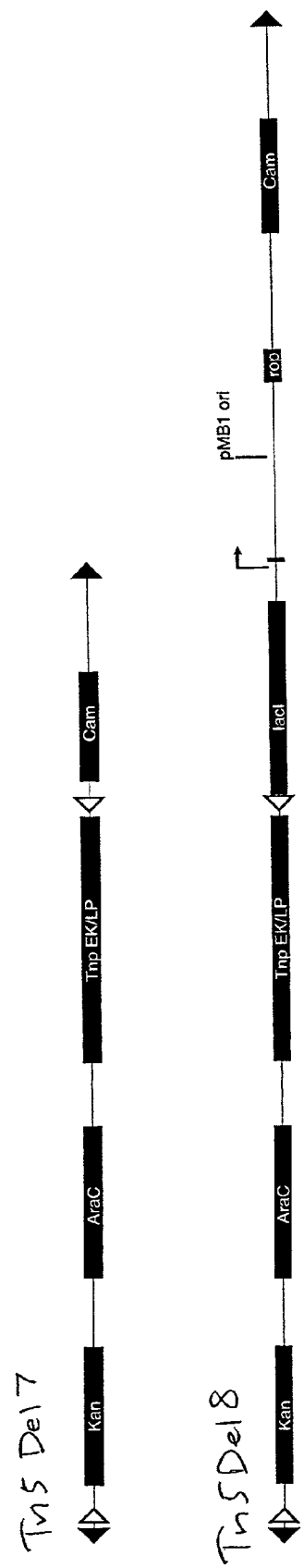
FIG. 9 depicts suitable transposons Tn5DEL7 and Tn5DEL8 for forming, respectively, deletions in a bacterial chromosome, and deletions in a bacterial chromosome while capturing the deleted portions in an extrachromosomal plasmid.

FIG. 9 depicts the transposons used in this Example. Transposon TnDEL7 was designed for inducing deletion of dispensible genetic material and does not have an origin of replication, thereby allowing the immediate isolation of deletions after induction. Transposon TnDEL8 contains a conditional (regulated) origin of replication and was used to maintain deleted genetic material in the cell on a plasmid until elimination is triggered, as described below. The selectable markers and other attributes of each transposon are as shown in FIG. 9. Both transposons Tn5DEL7 and Tn5DEL8 were cleaved from donor vectors pGT7 (SEQ ID NO:9) and pGT8 (SEQ ID NO:10), respectively, by restriction enzyme digestion using PshAI and were extracted from agarose gel using QIAquick Gel Extraction Kit (Qiagen).

Both transposons contain nested pairs of transposase-interacting sequences. The outer pair of sequences are Tn5 IE ends that can participate in forming synaptic complexes in the presence of Tnp1. The inner pair of sequences are ME artificial ends that can participate in transposition reactions in the presence of Tnp2. This efficient combination is preferred, as high transposition efficiency is important for effective screening without selection.

In the following trials, transposome synaptic complexes were introduced into cells by electroporation. $Km^R$ and $Cm^R$ colonies were selected. For Tn5DEL7, 50 to 80 percent of transposition events were recovered, with a quarter having deletions of desired orientation. For Tn5DEL8 the percent of successful deletion events exceeds 95%, presumably due to negative consequences of having two active origins of replication on the chromosome.

Depending upon the task, single colonies, or a pooled collection of about 50 colonies, were used to start liquid cultures. At an early exponential growth state, arabinose was added to induce a second transposition step. In the case of TnDEL8, chloramphenicol and IPTG were also added. IPTG maintains plasmids formed during deletion induction and to depress growth of cells in which the transpson-encoded ori did not excise from the chromosome during induction. This creates a selection against such cells. After a few hours, cells were sub cultured in the same media with 100-fold dilution and left shaking overnight. Then, cells were diluted and plated to yield single colonies for replica plating. $Km^S$, $Cm^S$ cells were picked in the case of TnDEL7 and $Km^S$ cells in the case of TnDEL8. In the latter case, plasmid DNA was prepared for analysis.

First, deletion size distribution was examined in the lactose operon region. This region was chosen for study since it is known to allow large deletions of at least 100 Kb (Bachmann, 1996). Tn5DEL7 was delivered as a synaptic complex into E. coli MG1655 cells that were then plated on Lactose-McConkey's medium with antibiotic selection. E. coli MG1655 with the deletion transposon inserted into the lac operon was isolated. A few white colonies were selected from thousands of red colonies. One colony was chosen for sequencing of the chromosomal DNA around the transposition site. The insert was located at 362,522-31 bp of the E.coli map. A single colony having the lac phenotype was selected and DNA sequencing was performed to determine the location of the insertion.

Then deletion formation was induced by induction of Tnp2 with arabinose and the deletions were collected by replica plating. Screening for deletions in the case of Tn5DEL7 was made by replica plating colonies on LB agar, LB-kanamycin (20 mg/L), and LB-chloramphenicol (20 mg/L). Cells sensitive to kanamicin were considered to have undergone transposition, and cells sensitive to both drugs were considered to have a deletion of adjacent DNA and the "right" portion of the transposon with only a small transposon linker being left on the chromosome.

Figure 10:
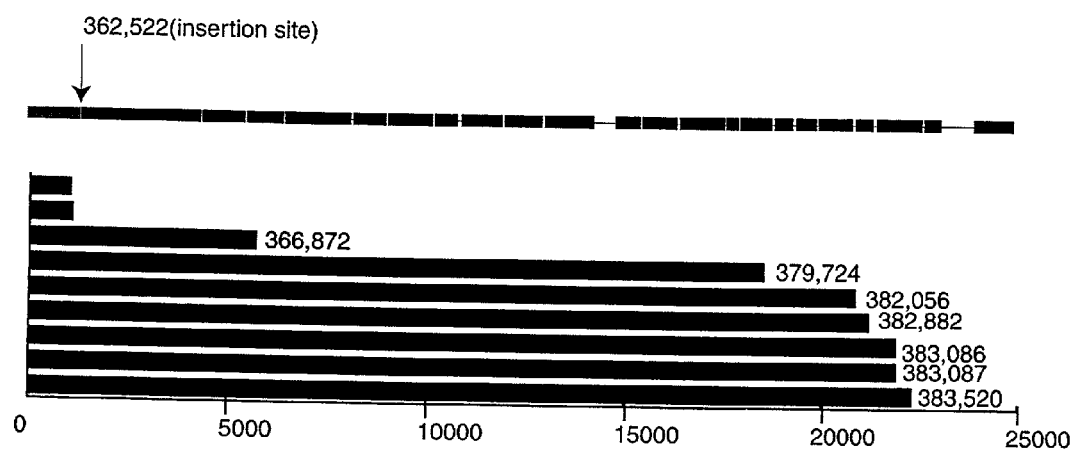
FIG. 10 depicts a set of bacterial chromosomal deletions induced in a method according to the invention.

A total of 9 independent deletions were analyzed by sequencing performed on ABI PRISM model 377, either directly from chromosomal DNA or by an inverse PCR technique. For lacZ insertion, direct chromosomal DNA sequencing was performed using primer FWD2: 5' CAGATCTCATGCAAGCTTGAGCTC 3' (SEQ ID NO: 5), complementary to the transposon linker. For sequencing deletions produced from this insertion, inverse PCR was performed with primers GGTCTGCTTTCTGA-CAAACTCGGGC (SEQ ID NO:6), and ACGC-GAAATACGGGCAGACATGGCC (SEQ ID NO:7) after digesting the chromosomal DNA with FspI and ligating. PCR products were purified from an agarose gel and sequenced with the standard Big Dye protocol. Of these nine deletions, two events were insertions within the transposon that resulted in loss of chloramphenicol resistance. The remaining seven were desirable events that deleted various lengths of chromosomal DNA. The summary of the sequencing analysis is shown in FIG. 10. The deletions vary in size from 4 to 23 Kb, with most deletions being about 20 Kb. The average deletion size is both surprising and encouraging. First, transposon attacking its own DNA is expected to find the target at a distance just beyond the persistence length, which is expected to be about 100 to 200 base pairs in the cell. Secondly, with deletions of this size, it is feasible to reach saturation (no further deletions without deleting essential genes), under conditions that permit repetitive application of the technology in a reasonable time frame.

Recursive Deletion Formation

Advantageously, all transposon components, apart from a short linker (64 bp), are lost after a deletion is generated using this system. The loss of the transposase gene ensures that the chromosome remains stable (in terms of subsequent transposition transposition). The loss of all selectable markers provides an opportunity to iteratively repeat the process.

Accordingly, 20 consecutive rounds of deletions were induced in MG1655 cells as follows. The protocol was applied repeatedly to mixtures of at least 10 independent deletions, thereby avoiding isolating deleterious deletions that result in delayed cell growth in a mixed culture. After 20 rounds, ten final strains having growth rates at least equal to that of the parental strain were obtained. After analyzing the new strains for the loss of metabolic activities, it was concluded that the strains are in part interrelated and in part independent.

To analyze the diversity and average size of deletions in these isolates, four isolates were digested with NotI and the digests were separated by pulse field electrophoresis using a CHEF-DR II BioRad system, according to the protocol of Heath et al., 1992, with minor technical modifications. The pattern for MG1655 matches that previously reported, and the identification letter for each fragment is shown at right. For each deletion strain, the pattern is altered and indicates a loss of DNA. The size of each new band in the four deletion strains was estimated by comparison to DNA markers. In some cases, bands seen in digested MG1655 DNA are absent, replaced in the isolates by shorter or longer fragments. The total amount of DNA deleted for four of the isolated strains was calculated as 250, 262, 100, and 247 kb. Thus an average deletion size per round is 11 kb, which agrees well with results obtained for the lactose operon region. It is assumed that the size of some deletions is limited by the presence of nearby essential genes. This suggests that large pieces of DNA can frequently be deleted during the first random chromosomal insertions. In other words, E. coli has significant excess DNA for growth in rich media. Second, 20 rounds are insufficient to saturate the chromosome with deletions.

Coupled Chromosomal Deletion/Plasmid Formation System.

The obvious limitation of the deletion formation system, described above is the inability to introduce deletions that involve essential genes. It would be advantageous to save deleted DNA conditionally in the same cell and to attempt to eliminate it later. Transposon Tn5DEL7 was, therefore, modified to include a conditional origin of replication, namely the origin from pAM34 (ATCC 77185). The conditional origin was easily controlled by IPTG, maintained moderate copy number, was lost relatively quickly under nonpermissive conditions, and was competent to accommodate large inserts. Importantly, the origin characteristically shows very low background on selective media with selection for the presence of drug resistance or essential gene. Only one or two colonies can arise on a plate lacking IPTG.

The protocol is as follows. Synaptic complexes were formed by mixing Tnp1 with precut Tn5DEL8 in binding buffer. Transposome complexes were assembled by incubation of precut transposon with Tnp1, 20 mM Tris Ac, 100 mM K Glutamate for 1 h at 37° C. Molar ratio was attempted to be 1:5, DNA: protein, with DNA concentration of 0.1 ug/ul.

The complexes were introduced into electrocompetent cells at standard recommended conditions (2.5 Kv, 5 mS). $Km^R$, $Cm^R$ colonies were selected in the first transposition selection. Individual colonies were inoculated into liquid media. At this point 0.4% arabinose and 1 mM IPTG were added and the cultures were aerated with shaking in 4 ml volume in 20 ml tubes at 37° C. Arabinose induces synthesis of Tnp2 and, hence, subsequent transposition events. IPTG supports maintenance of the plasmids containing DNA deleted from the chromosome. The cells of interest were kanamicin sensitive and chloramphenicol resistant, since replication of excised DNA circles was supported by keeping 1 mM IPTG in the media. Plasmids were detected in more then 90% of cases, indicating strong selection against active extra origin of replication on the chromosome.

Table 1 shows the final products obtained for 15 independent insertions of Tn5DEL8. The largest plasmid for each case was analyzed by sequencing to define the initial insertion position and the extent of deletion. To determine whether the deleted DNA in each plasmid was essential, cells were streaked on rich media with no IPTG. In the absence of IPTG, the extrachromosomal plasmid, which containing the excised sequences, is lost. In some cases individual colonies did not form, indicating a dependence on the plasmid. The simplest cases is isolate 12.17. Only gene dnaK is deleted; it is known to be essential. In isolate 14.17, one of two genes (rpoZ and gmk) is essential. For insertion #4 three plasmids were analyzed to define DNA carrying essential genes. The difference in size among the plasmids is minimal, but the difference in consequences of elimination of plasmids is dramatic. Plasmids 4.6 and 4.9 differ by two genes, glyS and glyQ. Although strain 4.6 can grow without IPTG, strain 4.9 cannot. Thus, at least one of the genes excised in isolate 4.9 is essential. With the exception of these genes, all other ORFs (complete or interrupted) can be considered non-essential (at least for growth in rich media).

For both strategies described here, deletions were obtained without direct selection as would be required for, e.g., SucB or GalK. That would require transposons to be larger and more importantly, would restrict the system to use with E. coli.

This Example demonstrates the proof of principle for creating a list of essential and nonessential bacterial genes. It is, accordingly, now technically possible to create a representative library of deletions/complementary plasmids covering a genome multiple times. Then systematic sequencing of deletion borders, in combination with tests of survival after eliminating the complementary plasmids can provide an extensive (ideally complete) set of genes that can be eliminated without detrimental consequences to the cell.

The present invention is not intended to be limited to the foregoing, but rather encompasses all such variations and modifications apparent to the skilled artisan that fall within the scope of the appended claims.

TABLE 1

| Insert # | Δ # | Insert End | ΔEnd | Size | Partial ORFs | Complete ORFs | Grow w/o IPTG |
|---|---|---|---|---|---|---|---|
| 1 | 1.3 | 1073109 | 1094823 | 21714 | b1028;b1012 | b1013;putA;putP;b1016–1018;ycdB;phoH;b1021–1025;tra5_3;b1027 | Y |
| 2 | 2.8 | 2776930 | 2770104 | 6826 | b2638;b2647 | b2639–b2646 | Y |
| 3 | 3.1 | 4407731 | 4403605 | 4126 | yjfI | yjeB;vacB;yjfH | Y |
| 4 | 4.2 | 3735047 | 3725227 | 9821 | yiaB | xylB;xylA;xylF;xylG;xylH;xylR;b3570 | Y |
| 4 | 4.6 | 3735047 | 3723521 | 11526 | none | yiaH;yiaA;yiaB;xylB;xylA;xylF;xylG;xylH;xylR;b3570 | Y |
| 4 | 4.9 | 3735047 | 3719490 | 15557 | yi5b | glyS;glyQ;yiaH;yiaA;yiaB;xylB;xylA;xylF;xylG;xylH;xylR;b3570 | N |
| 5 | 5.1 | 1224154 | 1210042 | 14112 | mcrA;minD | b1160–b1173;minE | Y |
| 6 | 6.2 | 3045069 | 3042244 | 2825 | bglA;gcvP | ygfF | Y |
| 7 | 7.1 | 2779269 | 2767042 | 12227 | b2633;b2647 | b2634–b2646 | Y |
| 8 | 8.4 | 3882592 | 3882500 | 92 | none | none | Y |
| 9 | 9.7 | 4589240 | 4595093 | 5853 | mdoB;tsr | yjjN;yjjM;b4356 | Y |
| 10 | 10.3 | 4141018 | 4117696 | 23322 | menA;frwC | hslU;hslV;ftsN;cytR;priA;rpmE;yiiX;metJ;metB;metL;metF;katG;yijE;yijF;gldA;talC;ptsA;yijI | N |
| 11 | 11.3 | 2793099 | 2795902 | 2803 | gabP;b2668 | ygaE;b2665–b2667 | Y |
| 12 | 12.17 | 14166 | 12088 | 2078 | none | dnaK | N |
| 13 | 13.19 | 4542104 | 4546611 | 4507 | fimC;fimH | fimD;fimF;fimG | Y |
| 14 | 14.17 | 3821524 | 3818998 | 2526 | spoT | rpoZ;gmk | N |
| 15 | 15.17 | 1570686 | 1544492 | 26194 | yddC;yddG | fdnG;fdnI;fdnI;b1477;b1478;sfcA;rpsV;b1481;osmC;b1483–1491;xasA;gadB | Y |

We claim:

1. A polynucleotide comprising:
   distinct first and second transposase-interacting repeat sequence pairs, each sequence pair having a first member and a second member provided in an inverted orientation relative to the first member, each sequence pair having a specificity for binding to and interacting with a distinct transposase enzyme, the first sequence pair flanking the second sequence pair; and
   a first sequence for conferring selectability upon a host cell, wherein the selectability conferring sequence is flanked by the first member of the first sequence pair and by the first member of the second sequence pair.

2. A polynucleotide as claimed in claim 1 wherein the first or second transposase-interacting inverted repeat sequence pair comprises Tn5 wild-type inside end sequences.

3. A polynucleotide as claimed in claim 1 wherein the first or second transposase-interacting inverted repeat sequence pair comprises Tn5 mosaic end sequences.

4. A polynucleotide as claimed in claim 1 wherein the first or second transposase-interacting inverted repeat sequence pair comprises Tn5 wild-type outside end sequences.

5. A polynucleotide as claimed in claim 1 further comprising between the members of the second inverted repeat sequence pair a second sequence for conferring selectability upon a host cell.

6. A polynucleotide as claimed in claim 5 further comprising, between the members of the second inverted repeat sequence pair, a polynucleotide that encodes a transposase that specifically binds to and interacts with the second sequence pair.

7. A polynucleotide as claimed in claim 6 further comprising an origin of replication flanked by the first member of the first sequence pair and by the first member of the second sequence pair.

8. A polynucleotide as claimed in claim 6 further comprising a preselected polynucleotide sequence insert flanked by the second member of the first sequence pair and by the second member of the second sequence pair.

* * * * *

UNITED STATES PATENT AND TRADEMARK OFFICE
CERTIFICATE OF CORRECTION

PATENT NO. : 7,067,644 B2
APPLICATION NO. : 10/007483
DATED : June 27, 2006
INVENTOR(S) : Igor Yu Goryshin et al.

Page 1 of 1

It is certified that error appears in the above-identified patent and that said Letters Patent is hereby corrected as shown below:

In the Specification

Column 1, Lines 15-18:
Delete the phrase:
"This invention was made with United States government support awarded by the National Institutes of Health, Grant No. GM50692. The United States has certain rights in this invention."

And replace with:
--This invention was made with government support under GM050692 awarded by the National Institutes of Health. The government has certain rights in the invention.--.

Signed and Sealed this
Fifteenth Day of December, 2020

Andrei Iancu
*Director of the United States Patent and Trademark Office*